(12) United States Patent
Duggan et al.

(10) Patent No.: US 9,238,831 B2
(45) Date of Patent: Jan. 19, 2016

(54) NUCLEIC ACID QUANTITATION METHOD

(75) Inventors: Karen Annette Duggan, New South Wales (AU); Hong Ha, New South Wales (AU); George Hodge, New South Wales (AU)

(73) Assignee: Accugen Pty Ltd, Rosebery (AU)

( * ) Notice: Subject to any disclaimer, the term of this patent is extended or adjusted under 35 U.S.C. 154(b) by 0 days.

(21) Appl. No.: 13/393,763

(22) PCT Filed: Sep. 2, 2010

(86) PCT No.: PCT/AU2010/001131
§ 371 (c)(1),
(2), (4) Date: May 21, 2012

(87) PCT Pub. No.: WO2011/026182
PCT Pub. Date: Mar. 10, 2011

(65) Prior Publication Data
US 2012/0231465 A1 Sep. 13, 2012

(30) Foreign Application Priority Data
Sep. 2, 2009 (AU) ................................ 2009904258

(51) Int. Cl.
*C12Q 1/68* (2006.01)
*C12P 19/34* (2006.01)

(52) U.S. Cl.
CPC .................................... *C12Q 1/6851* (2013.01)

(58) Field of Classification Search
None
See application file for complete search history.

(56) References Cited

U.S. PATENT DOCUMENTS

2007/0122818 A1    5/2007  Mazumder et al.
2011/0008328 A1*   1/2011  Bingham et al. ........... 424/133.1

OTHER PUBLICATIONS

Lee et al., "Absolute and relative QPCR quantification of plasmid copy number in *Escherichia coli*," Journal of Biotechnology, 2006, vol. 123, pp. 273-280.*
Napier, M. P., et al. "Antibody-directed Enzyme Prodrug Therapy: Efficacy and Mechanism of Action in Colorectal Carcinoma[1]," Clinical Cancer Research, 6:765-772 (Mar. 2000).
Shearer, P.L., et al. "A quantitative, real-time polymerase chain reaction assay for beak and feather disease virus," Journal of Virological Methods, 159(1):98-104 (Mar. 20, 2009).
International Search Report for PCT/AU2010/001131 dated Nov. 4, 2010.
Becker, Andreas, et al. "A Quantitative Method of Determining Initial Amounts of DNA by Polymerase Chain Reaction Cycle Titration Using Digital Imaging and a Novel DNA Stain," Analytical Biochemistry, 237: 204-207 (1996).
Peccoud, Jean. "La PCR quantitative: un nouvel outil pour l'analyse médicale," M/S Medecine Sciences, Societe Des Periodiques Flammarion, Paris, FR; 9(12): 1378-1385 (Dec. 1, 1993).
Vener, T., et al. "Quantification of HIV-1 Using Multiple Competitors in a Single-Tube Assay," Biotechniques; 21(2): 248-250, 252, 254-255 (Aug. 1996).
Whelan, Joseph A., et al. "A method for the absolute quantification of cDNA using real-time PCR," Journal of Immunological Methods; 278: 261-269 (2003).
Examination Reports for New Zealand Application No. 598876 dated Oct., 23, 2012; Feb. 14, 2013; and Dec. 17, 2013.
Office Action for Chinese Application No. 201080048692 dated Oct. 21, 2013.
Office Action for Korean Application No. 10-2012-7008496 dated Dec. 26, 2013.
Supplementary EP Search Report for EP Application No. 10 81 3163 dated Jun. 6, 2013.
Novoradovskaya, Natalia, et al. "Universal Reference RNA as a standard for microarray experiments," BMC Genomics, 5(20): 1-13 (2004).

* cited by examiner

*Primary Examiner* — Young J Kim
(74) *Attorney, Agent, or Firm* — Foley Hoag LLP; Thi K. Dio

(57) ABSTRACT

The present invention relates to methods of quantifying nucleic acids and in particular to an improved universal method of quantifying nucleic acids for gene expression studies without the need for normalising data to a housekeeping gene or to a synthetic gene of interest.

12 Claims, 14 Drawing Sheets

SEQUENCE LISTING

<160> NUMBER OF SEQ ID NOS: 32

<210> SEQ ID NO 1
<211> LENGTH: 24
<212> TYPE: DNA
<213> ORGANISM: Rattus rattus

<400> SEQUENCE: 1
aaagatggtg caccctgtgt cttc                                    24

<210> SEQ ID NO 2
<211> LENGTH: 22

```
<212> TYPE: DNA
<213> ORGANISM: Rattus rattus

<400> SEQUENCE: 2
tgcaactgct ttggaaggac tc                                              22

<210> SEQ ID NO 3
<211> LENGTH: 23
<212> TYPE: DNA
<213> ORGANISM: Rattus rattus

<400> SEQUENCE: 3
aaagatggtg caccctgtgt ctt                                             23

<210> SEQ ID NO 4
<211> LENGTH: 22
<212> TYPE: DNA
<213> ORGANISM: Rattus rattus

<400> SEQUENCE: 4
caggcaagtg cactggtatt tg                                              22

<210> SEQ ID NO 5
<211> LENGTH: 21
<212> TYPE: DNA
<213> ORGANISM: Rattus rattus

<400> SEQUENCE: 5
aatgctgtga ggagtgggtg t                                               21

<210> SEQ ID NO 6
<211> LENGTH: 23
<212> TYPE: DNA
<213> ORGANISM: Rattus rattus

<400> SEQUENCE: 6
catcccacag gtcttagaac agg                                             23

<210> SEQ ID NO 7
<211> LENGTH: 22
<212> TYPE: DNA
<213> ORGANISM: Rattus rattus

<400> SEQUENCE: 7
atgcaaaagg aaataactgc ac                                              22

<210> SEQ ID NO 8
<211> LENGTH: 20
<212> TYPE: DNA
<213> ORGANISM: Rattus rattus

<400> SEQUENCE: 8
ttgcttgctg atccacattt                                                 20

<210> SEQ ID NO 9
<211> LENGTH: 20
<212> TYPE: DNA
<213> ORGANISM: Rattus rattus

<400> SEQUENCE: 9
ttcctgggta tggaatcctg                                                 20

<210> SEQ ID NO 10
```

-continued

```
<211> LENGTH: 22
<212> TYPE: DNA
<213> ORGANISM: Rattus rattus

<400> SEQUENCE: 10
ggcatagagg tctttacgga tg                                              22

<210> SEQ ID NO 11
<211> LENGTH: 20
<212> TYPE: DNA
<213> ORGANISM: Rattus rattus

<400> SEQUENCE: 11
agagtcgtct ctgcatggtc                                                 20

<210> SEQ ID NO 12
<211> LENGTH: 21
<212> TYPE: DNA
<213> ORGANISM: Rattus rattus

<400> SEQUENCE: 12
gttttcctct aggtcagctt c                                               21

<210> SEQ ID NO 13
<211> LENGTH: 23
<212> TYPE: DNA
<213> ORGANISM: Rattus rattus

<400> SEQUENCE: 13
aagatggtgc accctgtgtc ttc                                             23

<210> SEQ ID NO 14
<211> LENGTH: 22
<212> TYPE: DNA
<213> ORGANISM: Rattus rattus

<400> SEQUENCE: 14
tgcaactgct ttggaaggac tc                                              22

<210> SEQ ID NO 15
<211> LENGTH: 23
<212> TYPE: DNA
<213> ORGANISM: Rattus rattus

<400> SEQUENCE: 15
aaagatggtg caccctgtgt ctt                                             23

<210> SEQ ID NO 16
<211> LENGTH: 22
<212> TYPE: DNA
<213> ORGANISM: Rattus rattus

<400> SEQUENCE: 16
caggcaagtg cactggtatt tg                                              22

<210> SEQ ID NO 17
<211> LENGTH: 21
<212> TYPE: DNA
<213> ORGANISM: Rattus rattus

<400> SEQUENCE: 17
aatgctgtga ggagtgggtg t                                               21
```

```
<210> SEQ ID NO 18
<211> LENGTH: 23
<212> TYPE: DNA
<213> ORGANISM: Rattus rattus

<400> SEQUENCE: 18
catcccacag gtcttagaac agg                                              23

<210> SEQ ID NO 19
<211> LENGTH: 23
<212> TYPE: DNA
<213> ORGANISM: Rattus rattus

<400> SEQUENCE: 19
tgcctggatg gggccgtggg ctg                                              23

<210> SEQ ID NO 20
<211> LENGTH: 23
<212> TYPE: DNA
<213> ORGANISM: Rattus rattus

<400> SEQUENCE: 20
aggggcagtc agggctgggc agg                                              23

<210> SEQ ID NO 21
<211> LENGTH: 23
<212> TYPE: DNA
<213> ORGANISM: Rattus rattus

<400> SEQUENCE: 21
tcggtgggtc cgtgtaccgc agc                                              23

<210> SEQ ID NO 22
<211> LENGTH: 23
<212> TYPE: DNA
<213> ORGANISM: Rattus rattus

<400> SEQUENCE: 22
tgggcaggcg cacgtccatg ctg                                              23

<210> SEQ ID NO 23
<211> LENGTH: 82
<212> TYPE: DNA
<213> ORGANISM: Rattus rattus

<400> SEQUENCE: 23
tcttccctcg ctctctggac ttatccactg acccagttct tgctgcccag aaaatcaaca     60
ggtttgtgca ggctgtgaca gg                                              82

<210> SEQ ID NO 24
<211> LENGTH: 90
<212> TYPE: DNA
<213> ORGANISM: Rattus rattus

<400> SEQUENCE: 24
tgtctgagac caactcaacc cagaaaaaca aaatggccct taactcttct gctgaagatg     60
gtatcaaaag aatccaagat gactgcccca                                      90

<210> SEQ ID NO 25
<211> LENGTH: 80
<212> TYPE: DNA
<213> ORGANISM: Rattus rattus
```

```
<400> SEQUENCE: 25
ctactgcttc agctccacag agaagaactg ctgtgtacgg cagctgtaca ttgactttag      60
gaaggacctg ggttggaagt                                                  80

<210> SEQ ID NO 26
<211> LENGTH: 98
<212> TYPE: DNA
<213> ORGANISM: Rattus rattus

<400> SEQUENCE: 26
ctgttggcga acaaatggcc tttattaaga aatggcttgc tcagggtaac tggtcagatt      60
tccacgagga agtgtttgct gcttctttga ctatgact                              98

<210> SEQ ID NO 27
<211> LENGTH: 120
<212> TYPE: DNA
<213> ORGANISM: Rattus rattus

<400> SEQUENCE: 27
tctgatgaac atacaccagt agaggatgaa gaaccaaaga aaagcactac ttcagcatct      60
agttcggaag atgataagaa gaagaaaagg aaatctagtc gttcaaaaga aagagccaag     120

<210> SEQ ID NO 28
<211> LENGTH: 90
<212> TYPE: DNA
<213> ORGANISM: Rattus rattus

<400> SEQUENCE: 28
tgtctgagac caactcaacc cagaaaaaca aaatggccct taactcttct gctgaagatg      60
gtatcaaaag aatccaagat gactgcccca                                       90

<210> SEQ ID NO 29
<211> LENGTH: 89
<212> TYPE: DNA
<213> ORGANISM: Rattus rattus

<400> SEQUENCE: 29
aagcaggcga agttttcatt cataaggata aaggctttat tcgcttggaa acacgaaccc      60
tagcggaaat tgccaaagtg gagctggac                                        89

<210> SEQ ID NO 30
<211> LENGTH: 95
<212> TYPE: DNA
<213> ORGANISM: Rattus rattus

<400> SEQUENCE: 30
ctggcacttt tactacttta gctgtttgct ttgtttgccc tttgctgttt ggttcaacct      60
tttcagtttt ccaccacact gcatttttct caccg                                 95

<210> SEQ ID NO 31
<211> LENGTH: 93
<212> TYPE: DNA
<213> ORGANISM: Rattus rattus

<400> SEQUENCE: 31
cccccaacct ttaccagcta ctcgaaccaa tcagcttgtc tgtagttgta tacacatcca      60
agcctgtggt tggtcagaag acaactttgt agg                                   93
```

```
<210> SEQ ID NO 32
<211> LENGTH: 90
<212> TYPE: DNA
<213> ORGANISM: Rattus rattus

<400> SEQUENCE: 32
gggtgtgcac agtgtttccc tgttcagcca tcccttgcaa actggagagt gacagtcatt      60
gcttgtggac agatcagatc ctcatgggct                                        90
```

NUCLEIC ACID QUANTITATION METHOD

FIELD OF THE INVENTION

The present invention relates to methods of quantifying nucleic acids and in particular to an improved universal method of quantifying nucleic acids for gene expression studies without the need for normalising data to a housekeeping gene or to a synthetic gene of interest. This method is applicable to diagnostic, forensic and research use, however, it will be appreciated that the invention is not limited to these particular fields of use.

BACKGROUND OF THE INVENTION

Any discussion of the prior art throughout the specification should in no way be considered as an admission that such prior art is widely known or forms part of the common general knowledge in the field.

PCR technologies for quantification of gene expression have improved through the development of rapid thermocylers and the introduction of fluorescence monitoring of amplified products after each cycle (real-time PCR). Quantification of gene expression occurs through the use of dyes, particularly fluorescent dyes, and the detection of increasing fluorescence during the exponential phase of PCR amplification proportional to the amount of nucleic acids in the sample at the beginning of the reaction. Quantification is based on the threshold cycle, i.e. the first cycle with detectable fluorescence, and can be performed in absolute manner with external standards (usually a synthetic gene) or in relative manner with a comparative normalizing reference gene serving as an internal calibrator (i.e. housekeeping gene). Control genes or housekeeping genes are used to normalise mRNA levels between different samples.

It is critical that the selected reference gene does not fluctuate since even marginal variations in gene expression will alter the relative quantification profile of the target gene. Pipetting and dilution errors also alter the level of amplification and thus alter the quantification profile.

Genes such as glyceraldehyde -3-phosphate dehydrogenase (GAPDH), porphobilinogen desaminase (PBGD), beta 2-microglobin or beta-actin are often used as internal calibrators in real-time PCR. However, the aforementioned genes have been shown to move in response to experimental conditions or treatments. Genes that are abundantly expressed, such as 18S, are also not ideal reference genes as PCR conditions need to be restricted so as not to swamp the reaction.

Thus, suitable housekeeping genes should be adequately expressed in the tissue of interest, and most importantly, show minimal variability in expression between the samples and under the experimental conditions or treatments used.

Many of these control genes however can show unacceptable variability in expression. It has been shown that the expression level of such genes may vary among tissues or cells and may change under certain circumstances i.e. different treatments. Thus it is crucial to validate housekeeping genes in any new experimental system. It is often a time consuming and difficult task to find a housekeeping gene or reference gene that is suitable for use in a specific experimental system. In some situations this may not be possible.

The use of external standards (i.e. a synthetic sequence) in gene expression studies generally requires that the gene of interest be cloned to provide the synthetic reference gene. In this method, known amounts of the synthetic reference gene sequence are serially diluted then subjected to amplification to produce a standard curve. Production of the cloned sequence for this method is generally a time consuming, labour intensive task and dilution errors are amplified exponentially which can lead to inaccurate assessment of nucleic acid levels. Stability and preservation of highly diluted cloned sequences can also cause difficulties.

Thus, there remains a need for a quick and efficient universal method of quantifying nucleic acids, that is applicable to any experimental situation or treatment condition, that does not require the use of a housekeeping gene or a synthetic gene of interest to normalise data.

It is an object of the present invention to overcome or ameliorate at least one of the disadvantages of the prior art, or to provide a useful alternative.

SUMMARY OF THE INVENTION

In a broad aspect, the present invention relates to a method for quantifying nucleic acids that does not require the use of a housekeeping gene or synthetic reference gene to normalize nucleic acid expression data. Rather the method of the present invention utilizes a universal reference oligonucleotide (or may use one or more such oligonucleotides) in combination with a suitable dye, which can be used to generate a standard curve from which the absolute level of an amplified target nucleic acid in a sample can be calculated. Thus, the method of the present invention can make use of the same reference oligonucleotide to quantify different nucleic acids of interest, either individually or in a mixture of such nucleic acids of interest.

The present invention also relates to kits for use in the method of the invention.

In a first aspect, there is provided a method for quantifying a target nucleic acid comprising:
  a) labelling a reference oligonucleotide having a predetermined length with a detectable marker;
  b) generating a standard curve using serial dilutions of the labelled reference oligonucleotide by plotting the intensity of the detectable marker against concentration of labelled reference oligonucleotide;
  c) amplifying a target nucleic acid in the presence of a detectable marker which labels the amplified target nucleic acid,
  d) comparing the intensity of the detectable marker associated with the labelled amplified target nucleic acid, with the standard curve and determining the quantity of the amplified target nucleic acid.

In a second aspect, there is provided a method for quantifying a target nucleic acid comprising:
  a) labelling a reference oligonucleotide having a predetermined length with a detectable marker;
  b) generating a standard curve using serial dilutions of the labelled reference oligonucleotide by plotting the intensity of the detectable marker against concentration of labelled reference oligonucleotide;
  c) amplifying a target nucleic acid;
  d) labelling the amplified target nucleic acid with a detectable marker;
  e) comparing the intensity of the detectable marker associated with the labelled amplified target nucleic acid, with the standard curve and determining the quantity of the amplified target nucleic acid.

The reference oligonucleotide sequence need not have any homology with the target nucleic acid or with any housekeeping gene sequence. However, because of the particular way in which the reference oligonucleotide is used in the method of the present invention (i.e. to prepare a standard curve following serial dilution of the reference oligonucleotide) the reference oligonucleotide sequence can have a degree of homology or even identity with a target nucleic acid sequence or a housekeeping gene, or smaller parts thereof. An advantage of the present invention is that the method can make use of the same single reference oligonucleotide to quantify different target nucleic acids. In practice the reference oligonucleotide may be a universal one, with a particular fixed length and GC content, typically an oligonucleotide of 100 bp and 50% GC content.

Preferably, the amplification of the target nucleic acid is performed by Polymerase Chain Reaction (PCR) method. Typically the target nucleic acid is amplified over 15 cycles but this is not critical to the method of the present invention. Simultaneous amplification of multiple target nucleic acids of interest in one reaction can also be performed (i.e. multiplex PCR).

The reference oligonucleotide may be of the same or similar length to the target nucleic acid sequence but this need not be so. The reference oligonucleotide may be longer or shorter than the target nucleic acid. Preferably a single standard curve is prepared with a single reference oligonucleotide and used for multiple target nucleic acid amplifications and quantifications. The multiple target nucleic acid amplifications and quantifications can each be performed at different times if desired.

Preferably the detectable marker is a dye that binds to dsDNA and it may be an intercalating dye. Preferably, the dye is a fluorescent dye. The dye used can be selected from any one of SYBR green I, SYBR green II, CYBR gold, Evagreen, oxazole yellow, thiazole orange, picogreen, TOTO or BEBO, Deep Purple™ however the choice of dye is not critical as other suitable dyes can also be used and would be known to those skilled in the art. Preferably the dye stoichiometry is one to one, but may be higher.

In a third aspect, there is provided, a kit for use in the method of the first or second aspect, comprising one or more reference oligonucleotides and a fluorescent dye. Preferably, only one reference oligonucleotide is present in the kit. If more than one oligonucleotide is present, each may have the same or different length.

In a fourth aspect, there is provided, a kit for use in the method of the first or second aspect, comprising one or more reference oligonucleotides labelled with a fluorescent dye.

In a fifth aspect, there is provided, a kit for use in the method of the first or second aspect, comprising serial dilutions of one or more reference oligonucleotides labelled with a fluorescent dye.

The reference oligonucleotide will preferably have a length greater than 60 bp and would typically be in the range between about 60 bp and about 170 bp. Most preferably the reference oligonucleotide will have the length of 100 bp, which can be used to quantify target nucleic acids, which are commonly in the range between about 60 to about 210 bp in length. The upper limit of length of the reference oligonucleotide is not critical and will be governed by practical considerations.

It is desirable that the GC content of a reference oligonucleotide is 45% or above. Typically, the GC content of the reference oligonucleotide may be selected in the range of about 45% to about 75% and most preferably it is 50%. The upper limit of GC content is not critical.

The reference oligonucleotide may be obtained from a biological source, natural or otherwise, using known techniques, or it may be prepared synthetically.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

DEFINITIONS

Figure 1:
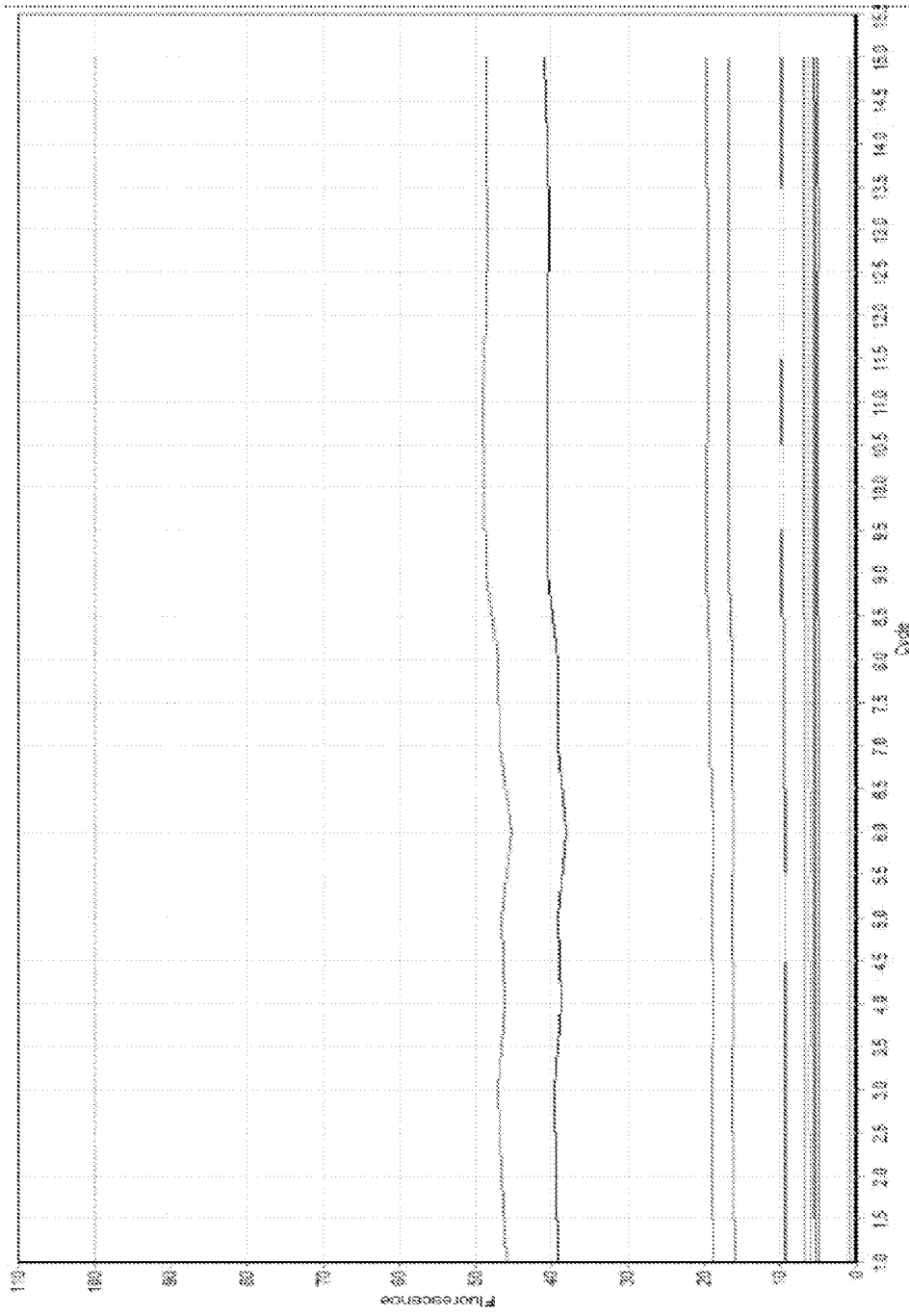
FIG. 1: Fluorescence of reference oligonucleotide standard at varying concentrations over 15 cycles. Each horizontal line represents one concentration. The lack of enzyme in the reaction mix ensures that the fluorescence is unchanged over numerous cycles. The graph further indicates the stability and reproducibility of the reference oligonucleotide dye complex through repeated denaturing and annealing cycles.

The term/phrases "gene" or "target nucleic acid" or "target gene" or "gene of interest" or "target sequence of interest" or "target of interest" or "nucleic acid of interest" as used herein have been used interchangeably and refer to the same concept.

The term "nucleic acid" refers to molecules that are composed of chains of monomeric nucleotides. As used herein the term is intended to encompass DNA, RNA and their variants and derivatives.

A "gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. The term "gene" may also encompas cDNA corresponding to the coding regions (e.g., exons) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

"Amplification" of nucleic acids sequences may be conveniently accomplished by Polymerase Chain Reaction (PCR) but may also be accomplished by another suitable method such as ligase chain reaction. In the context of the present specification the terms "Polymerase Chain Reaction" and its acronym "PCR" are used according to their ordinary meaning as understood by those skilled in the art. Examples of PCR methods can be found in common molecular biology textbooks and reference manuals used in the art. For example PCR Technology: Principles and Applications for DNA Amplification (1989) Ed H A Erlich. Stockton Press, New York. In order to optimise the PCR amplification, the primers can be used at different concentrations and ratios. Selection of these and other variables would be appreciated and obtainable by persons skilled in the art.

"Amplicon" in the context of the present invention refers to pieces of DNA or nucleic acid products that are formed by amplification reactions such as those performed by PCR or ligase chain reactions. In one context, the amplicon may be the product of the "target nucleic acid" or "gene of interest" or "nucleic acid of interest", etc.

"Primer" can be used interchangeably with "oligonucleotide", and can be natural, synthetic, or a modification thereof and capable of acting as a point of initiation of nucleotide synthesis sufficiently complementary to a specific nucleotide sequence on a template molecule.

The "reference oligonucleotide" or "reference nucleic acid sequence" or "universal reference oligonucleotide" as used in the context of the present invention is a nucleic acid, preferably double stranded DNA, and encompasses any suitably sized nucleic acid useful in the preparation of a standard curve, or otherwise suitable for quantification of target nucleic acids of interest. Hence, the reference oligonuclotide can be a polynucleotide but may also be a shorter sequence. Suitable reference oligonucleotide characteristics are described herein.

The reference oligonucleotide may be entirely synthetic or may be obtained from natural sources of DNA using a suitable restriction enzyme to obtain a suitable size nucleic acids as a reference oligonucleotide.

To obtain suitably large quantities, the reference oligonucleotide may be amplified using an amplification reaction (e.g. PCR or ligase chain reaction) or may be expressed recombinantly in a microorganism and purified before use. If size of the reference oligonucleotide permits it can also be prepared in quantity by synthetic means.

A "housekeeping gene" is typically a constitutive gene that is required for the maintenance of basal cellular function. Such genes are found in all cells. Some housekeeping genes are expressed at relatively constant levels however other housekeeping genes may vary in expression depending on experimental conditions used.

A "standard curve" is a quantitative research tool, a method of plotting assay data that is used to determine the absolute concentration of a substance such as DNA and proteins.

"Quantification" as used in the context of the present invention means detecting the absolute amount of a substance, in the present case the "target gene of interest".

"Serial dilution" refers to any form of dilution necessary to prepare a standard curve covering a range of concentrations of a substance (e.g. nucleic acid) from which the amount of a "target nucleic acid" can be quantified.

In the context of the present invention "dsDNA" refers to double stranded DNA, "bp" refers to base pairs, "dNTP's" refers to deoxynucleotide triphosphate, "RNA" refers to ribonucleic acid, "tRNA" refers to transfer RNA, "rRNA" refers to ribosomal RNA, "siRNA" refers to small interfering RNA, "miRNA" refers to micro RNA, "mRNA" refers to messenger RNA and "cDNA" refers to complementary DNA.

The "GC content" of a nucleic acid sequence such as a primer has an effect on various properties of a primer including its melting temperature (Tm).

PREFERRED EMBODIMENT OF THE INVENTION

The present invention has been motivated by the lack of accurate and efficient means for quantifying nucleic acid expression in control and treatment animal/human groups. It has also been motivated by the fact that most of the known housekeeping genes used in gene expression studies, move in response to experimental conditions or treatments, thus skewing results.

An advantage of the present invention is that the described methods dispose of the need for housekeeping genes or synthetic reference genes used to normalise data and quantify gene expression. Another advantage of the present invention is that amplification of a target nucleic acid, usually by PCR but other methods may be used, can be performed over a reduced number of cycles (e.g. 15 cycles) rather than the usual 30 cycles or so, used for gene expression studies, thus providing sufficient amount of target nucleic acids for use in the quantification assay while significantly reducing the time and cost of the assays.

In the novel approach described herein, a dye in combination with a reference oligonucleotide of a predetermined length, which advantageously may be unrelated to the target nucleic acid of interest, but may also be similar or identical to the gene of interest, is used to generate a standard curve. The standard curve is generated by serially diluting a fluorescently labelled reference oligonucleotide according to the invention and plotting the intensity level of the fluorescent dye vs. concentration of labelled reference oligonucleotide. No amplification of the reference oligonucleotide is necessary to produce the standard curve. This contrasts with current methodologies for assessing gene expression whereby the test sample and the housekeeping gene/synthetic reference gene are both amplified either side by side or combined in one reaction mixture.

The same standard curve, once prepared, can be used numerous times if required to quantify more than one target nucleic acid of interest. The diluted reference oligonucleotide solutions used for the preparation of standard curve are stable over time, for example over a period of about one month, and repeated freezing and thawing of the solutions. This enables the preparation and storage of reference oligonucleotide solutions ahead of any experimental requirements.

The reference oligonucleotide can be a fully synthetic sequence, an amplified sequence (e.g. PCR generated), or a suitable size restriction fragment of a larger nucleic acid isolated from a natural source. The reference oligonucleotide used in the methods of the present invention is not what is described as a "housekeeping gene" or a "synthetic reference gene", i.e. it does not need to be amplified along with the gene of interest.

It may be desirable to design reference oligonucleotides of different lengths to prepare standard curves for quantifying target nucleic acids of different lengths, but this is not critical for the method of the present invention. However, a particular advantage of the present invention is that a single reference oligonucleotide of a particular fixed length may be used in a standard curve to quantify target nucleic acids which are either longer or shorter than the reference oligonucleotide, as well as having different nucleic acid sequences.

The reference oligonucleotide will desirably have a length greater than 60 bp and would typically be in the range between about 60 bp and about 170 bp (i.e. about 60, 70, 80, 90 100, 110, 120, 130, 140, 150, 160 or about 170 bp), which can be used to quantify target nucleic acids in the range between about 80 to about 210 bp in length, more typically in the range between about 80 and about 150bp in length. Further, any reference oligonucleotide having a length in the range stated above can be used to quantify any one or more target nucleic acid products of length in the range stated above. It will be understood that the length of the target sequence is immaterial to the method of the present invention as it is selected as a nucleic acid of interest (or multiple nucleic acids of interest) by those using the method.

The upper limit of length of the reference oligonucleotide is not critical and will be governed by practical considerations. Thus, a reference oligonucleotide larger than 170 bp may be used, if desired, in the method of the present invention without deleterious effects on quantification of a target nucleic acid (e.g. lengths of between about 170-180, 180-200, 200-220, 220-240, 240-260, 260-280, 280-300, 300-320, 320-340, 340-360, 360-380, 380-400 bp etc.).

It is desirable that the GC content of a reference oligonucleotide is 45% or above. The upper limit of GC content is not critical. Thus, reference oligonucleotides with 75% GC content yielded similar results to reference oligonucleotides having lower GC content. Typically, the GC content of the reference oligonucleotide may be selected in the range of about 45% to about 75% (eg. from about 45%, 50%, 55%, 55%, 60%, 65%, 70% or about 75%).

The reference oligonucleotide sequence need not have any homology with the target nucleic acid or with any housekeeping gene sequence. However, because of particular way in which the reference oligonucleotide is used in the method of the present invention (i.e. to set up a standard curve following serial dilution of the reference oligonucleotide) the reference oligonucleotide sequence can have a degree of homology or even identity with a target nucleic acid sequence or a housekeeping gene, or smaller parts thereof. An advantage of the present invention is that the method can make use of the same reference oligonucleotide to quantify different target nucleic acids. In practice the reference oligonucleotide will be a universal one, with a particular fixed length and GC content, typically an oligonucleotide of 100 bp and 50% GC content. It is envisaged that at least three different reference oligonucleotides in the ranges described above are included in a kit in order to be able to quantify the full range of gene (nucleic acid) sizes that would commonly be measured.

If a reference oligonucleotide is obtained from a biological source, natural or otherwise, using a restriction enzymes to obtain a fragment of a suitable size, the GC content can be determined using standard molecular biology techniques well known to those skilled in the art and would not require more than simple analytical procedures to select and determine a fragment of a suitable size (Sambrook et al. Molecular Cloning: A Laboratory Manual, 2nd ed. (1989) Cold Spring Harbor Laboratory Press, Cold Spring Harbor, N.Y.). Synthetic reference oligonucleotides may also be conveniently used and may be simply prepared by known techniques such as for example those described in Sambrook et al. Molecular Cloning: A Laboratory Manual, 2nd ed. (1989) Cold Spring Harbor Laboratory Press, Cold Spring Harbor, N.Y. and Roe et al. DNA Isolation and Sequencing" (Essential Techniques Series) (1996) John Wiley & Sons, Inc., N.Y. The desired length and GC content of a synthetic reference oligonucleotide can be easily selected during synthesis.

The method of the invention is suitable for use with intercalating dyes as well as fluorescent probes (dyes). For intercalating dyes, the length of the reference oligonucleotide does not affect the intensity of fluorescence for a given concentration of the reference oligonucleotide, as long as the length of the reference oligonucleotide is 60 bp or longer. There appears to be no upper limit of reference oligonucleotide length which impacts on intensity of fluorescence. As a consequence one reference oligonucleotide is suitable for use as a reference standard for any number of nucleic acid target sequences of interest that may have different lengths, GC content and/or nucleotide sequence. For fluorescent probes, the same reference oligonucleotide can be used for numerous nucleic acid targets studied serially provided the same fluorphore is used. Alternatively multiple standard curves can be generated using one reference oligonucleotide but differing fluorophores to provide a quantitative framework for multiplex rt-PCR products.

Thus, the method of the present invention is advantageous as it disposes of the need to amplify a housekeeping gene and constantly run assays for housekeeping genes or synthetic reference genes to normalize nucleic acid expression data within each experiment. One standard curve can be prepared and used over a period of time to quantify more than one target nucleic acid of interest, which can vary in size and sequence, thereby cutting the cost and time when compared to conventional gene expression assays.

The methods of the present invention lend themselves to automation as well as monitoring target nucleic acid amplification and quantification in real time by storing the reference oligonucleotide standard curve information in a computer based system prior to commencement of amplifying the target nucleic acid of interest and either taking samples of the amplification reactions at certain time periods or monitoring increase in fluorescence over time (real time) and relating the information to the stored standard curve information. When operating the methods in such a mode a standard curve may be generated periodically, e.g. weekly or monthly, and this information stored and used to quantify target nucleic acids of interest over a period of time without the need to prepare new standard curves.

The method and kit of the present invention can be advantageously used to quantify genes (nucleic acids) of interest having gene (nucleic acid) products which are commonly encountered in analytical and research laboratories and are usually in the range of 80 to 150 bp in length and having from 30% to 60% GC content, using a single reference oligonucleotide. More particularly, method and kit of the present invention is useful in quantifying nucleic acid products which exceed 60 bp in length and 35% GC content using a single reference oligonucleotide which preferably is 100 bp in length and has 50% GC content. The preferred format of the kit thus consists of such a reference oligonucleotide or its serial dilutions and the dye or other suitable detectable label used in the reaction for the nucleic acid of interest. Alternatively, the kit includes a reference oligonucleotide labelled with a dye or other suitable marker, or serial dilutions of such labelled reference oligonucleotide, and the dye or marker to be used for labelling the nucleic acid of interest.

As a general guide for preparing a standard curve to be used in the method of the present invention, the reference oligonucleotide is serially diluted in duplicate using the same reaction buffer as that used for the gene of interest, to give final amounts, for example, in the range from about 0.01 to about 10 pmol (can be a narrower or broader range) of reference oligonucleotide per reaction tube, to enable construction of a standard (reference) curve as described herein. The range of concentrations of the reference nucleotide is determined by simple trial and error, depending on the requirements. A detectable marker such as a fluorescent dye (same as that used for the gene of interest and in the same amount as that used for the gene of interest reaction) is then added to each reaction tube. Typically, the reaction tubes undergo 15 cycles (can be more cycles if desired) in a real time rt-PCR machine, the cycling conditions reflecting those used for the gene of interest. Thus, if the initial denaturation conditions for the gene of interest are, for example, 94° C. and 2 minutes, the tubes containing the serial dilutions of the reference oligonucleotide (to be used to construct the standard curve) undergo initial denaturation at 94° C. for 2 minutes. The next 15 cycles then parallel those of the gene of interest, so that if the gene of interest cycling conditions include, for example, denaturation at 95° C. for 30 seconds followed by annealing at 60° C. for 30 seconds, the tubes containing the serial dilutions of the reference oligonucleotide are also cycled at 95° C. for 30 seconds (denaturation) and 60° C. for 30 seconds (annealing). If a fluorescent dye is used as a label or marker, fluorescence can be acquired during each annealing phase as demonstrated in FIGS. 1 and 2. A standard (reference) curve of fluorescence vs. amount of nucleic acid (for example DNA) is then constructed as described herein.

Although the invention has been described by way of example, it should be appreciated that variations and modifications may be made without departing from the scope of the invention. Furthermore, where known equivalents exist to specific features, such equivalents are incorporated as if specifically referred to in this specification.

EXAMPLES

Example 1

Calculations

In rt-PCR after a predetermined number of cycles (c) the amount of gene of interest present (R) is related to the amount of that gene present at the commencement of the PCR amplification (n) in a reproducible fashion, if the efficiency of replication is 100% and at each cycle each copy of the gene is replicated.

$R = n \times 2^c$ n=replicates present at time 0
c=number of cycles at a predetermined fluorescence
R=Replicates present after c cycles When efficiency is less than 100%: and not all copies of a gene are replicated at each cycle and the equation is modified to take account of this decrease in efficiency of replication, then $R = n \times e^c$ e=efficiency of replication
c=number of cycles at a predetermined fluorescence
R=Replicates present after c cycles Example 2

Preparation of Reference Oligonucleotides

Although the example cited uses RNA for connective tissue growth factor (CTGF) to generate the reference oligonucleotides, it should be appreciated that reference oligonucleotides for use as standards can be generated from RNA for any gene or to coding or non-coding DNA.

Reference oligonucleotides of 70, 90 and 170 base pairs in length were prepared by amplification of segments of the CTGF gene from heart tissue of spontaneous hypertensive rats (SHR) as follows:

1) RNA Extraction

Tissues was collected from SHR animals for total RNA extraction by phenol and guanidine isothiocyanate (Chomczynski and Sacchi 1987) with modification. Liquid nitrogen frozen SHR hearts were homogenised by a Mixer Mill MM300 (Retsch GmbH, Germany). The cryogenic samples, each of 100 mg, were added to 1 mL Trizol Reagent (Invitrogen) in a 1.5 mL Safe-Lock micro test tube (Eppendorf Biopur, Hamburg, Germany) with Tungsten Carbide Beads 3 mm (Qiagen) and ground at a frequency of 30 Hz. RNA extraction then followed according to the manufacturer's recommendations (Invitrogen). After samples were disrupted for RNA, phase separation was proceeded whereby 200 mL of chloroform (Lab-Scan Analytical Sciences, Lomb Scientific, Taren Point, NSW, Australia) was added, and the sample shaken vigorously by hand for 15 seconds and then incubated at room temperature (23-30° C.) for 5 minutes prior to centrifugation at 12,000 rpm (13,201 g) for 20 minutes at 4° C. (brake off), using a Sigma 1-15PK centrifuge (John Morris Scientific, Chatswood, NSW, Australia). 300 mL of the upper aqueous phase was collected into a fresh 1.5 mL eppendorf tube and 500 mL of pre-cooled propan-2-ol (isopropanol) (Lab-Scan Analytical Sciences, Lomb Scientific, Taren Point, NSW, Australia) was added, and the sample inverted by hand a few times to mix. The mixture was incubated at room temperature for 10 minutes to precipitate RNA. A pellet was formed by centrifugation at 12,000 rpm for 20 minutes at 4° C. (John Morris Scientific, Chatswood, NSW, Australia). The supernatant was discarded, and the pellet then washed with 1 mL of 75% (v/v) absolute molecular grade ethanol (Lab-Scan Analytical Sciences, Lomb Scientific, Taren Point, NSW, Australia) diluted in diethyl pyrocarbonate (DEPC) (Sigma-Aldrich, Castle Hill, NSW, Australia) and spun at 10,000 rpm for 10 minutes at 4° C. (John Morris Scientific, Chatswood, NSW, Australia). The pellet was collected and air dried for a few minutes in a fume hood then dissolved in DEPC-treated Milli-Q water and stored at −80° C. Total RNA concentration was determined by spectrophotometer absorbance, using the Nanodrop 1000 (Nd-1000, Thermo Scientific) at 260 nm ($A_{260}$); and the purity of the RNA was considered satisfactory if the ration of $A_{260}$:$A_{280}$ was about 2.0.

2) Deoxyribonuclease 1 (DNase-1) Treatment

RNA samples were treated with DNase-1 (Invitrogen) prior to reverse transcription-polymerase chain reaction (RT-PCR) to eliminate double and single stranded DNA. In 0.5 mL DNase and RNase-free eppendorf tubes, up to 1 μg RNA was digested with 1 unit/μL DNase-1 and 1 μL of 10×DNase-1 Reaction Buffer in a total volume of 10 μL with DEPC-treated water. The samples were incubated for 15 minutes at room temperature prior to inactivating DNase-1 by chelating calcium and magnesium ions with 1 μL of 25 mM EDTA in the solution mix and heating at 65° C. for 10 minutes. The samples were chilled on ice and stored at −80° C. All the components of the mix were supplied in the DNase-1 kit (Invitrogen).

3) Assessment of RNA Quality and Concentration

DNase-1 treated RNA samples were analysed on the MCE-202 MultiNA microchip automated electrophoresis instrument (Shimadzu Biotech, Rydalmere, NSW, Australia) for purity, size and concentration of ribosomal RNA (rRNA) 18S and 28S subunits. All steps were carried out according to the manufacturer's recommendation, with minor modifications. Briefly, 3 μL of each sample was mixed with an equal volume of internal RNA marker (Shimadzu Biotech, Rydalmere, NSW, Australia) in a 96-well plate and sealed with adhesive PCR aluminium foil (Thermo Scientific, Integrated Sciences, NSW, Australia). The RNA along with internal standard markers of known concentration and size, (lower and upper molecular size markers), automatically correct electrophoresis results for automatic size prediction and quantitation of RNA samples. The RNA-6000 ladder (Applied Biosystems, Victoria, Australia) was diluted with DEPC-treated water at a ratio of 1:5 (v/v); the solution mixture was then mixed with RNA marker solution at 1:1 (v/v). Both, samples and ladder mixtures, were heat denatured at 65° C. for 5 minutes and immediately chilled on ice for 5 minutes. These size range separation were preformed on the MultiNA's microchips (Shimadzu Biotech, Rydalmere, NSW, Australia) in RNA Separating Buffer (Shimadzu Biotech, Rydalmere, NSW, Australia) containing 10,000× fluorescent intercalating dye SYBR Green II (Invitrogen), diluted 1:99 with TE (10 mM Tris-HCl, 1 mM disodium EDTA, pH8.0) (Sigma-Aldrich), and 20% (v/v) formamide (Invitrogen).

4) Reverse Transcription

First strand complementary DNA (cDNA) was synthesised from a single stranded RNA template using Moloney-Murine Leukaemia Virus Reverse Transcriptase (M-MLV RT) of the SuperScript III First-Strand Synthesis SuperMix kit (Invitrogen) according to manufacturer's instructions. All reactions were carried out in 0.2 mL thin-walled eppendorf tubes; and all incubation steps were performed on a Rotor-Gene 6000 (Corbett Research, Sydney, Australia; Qiagen). Up to 5 μg of total RNA was heat denatured at 65° C. for 5 minutes with 1 μL of 50 μM oligo $(dT)_{20}$ and 1 μL of Annealing Buffer in a total volume of 8 μL with DEPC-treated water. The samples were chilled on ice for at least 1 minute before added to 10 μL of 2× First-Strand Reaction Mix and 2 μL SuperScript III/RNaseOUT Enzyme Mix. The sample was briefly vortexed to mix, and then collected by pulse spinning then incubated at 50° C. for 50 minutes for cDNA synthesis. The RT enzyme was denatured to terminate the reaction at 85° C. for 5 minutes, and the sample was immediately chilled on ice and stored at −20° C. Negative control samples without RT enzyme or RNA were included to verify the absent of DNA contamination.

5) Primers

Primer pairs generating PCR product lengths of 70bp, 90bp and 170bp were designed based on sequences published by NCBI GenBank for rat mRNA for connective tissue growth factor (CTGF) (Accession number AB023068). The primer sequences (primer sequences themselves being 21-24 bases in length) were sent off for synthesis (Invitrogen) as desalted lyophilised products. The primers were reconstituted to a concentration of 50μM, with TE (10mM Tris-HC1, pH8.0, 1mM EDTA) (Invitrogen) and stored at −20° C.

TABLE 1

Primer sequences for rat CTGF

| Sense Sequences (5'-3') | Antisense Sequences (5'-3') | mRNA Range | Product Size (bp) |
|---|---|---|---|
| AAAGATGGTGCACCCTGTGTCTTC (SEQ ID NO: 1) | TGCAACTGCTTTGGAAGGACTC (SEQ ID NO: 2) | 499-568 | 70 |
| AAAGATGGTGCACCCTGTGTCTT (SEQ ID NO: 3) | CAGGCAAGTGCACTGGTATTTG (SEQ ID NO: 4) | 499-588 | 90 |
| AATGCTGTGAGGAGTGGGTGTG (SEQ ID NO: 5) | CATCCCACAGGTCTTAGAACAG (SEQ ID NO: 6) | 683-852 | 170 |

Reference oligonucleotides varying in length from 50 to 170 base pairs and in GC content from 40 to 75% were formulated from various sections of CTGF, α Actin and β Actin.

Reference oligonucleotides were prepared as described under Example 2 and standard curves prepared as described under Example 3. Primers generating the reference oligonucleotides (50 to 170bp) were designed based on sequences published by the NCBI Genbank for rat mRNA for CTGF (Accession No. AB023068) and rat mRNA for αActin and βActin (Accession No. NM 019183 and BC 063166 respectively), See Table 2.

6) PCR

PCR was performed on SHR hearts, with each primer set to determine different concentration of dsDNA binding to fixed amount of EvaGreen. All reagents used in this PCR were bought from Invitrogen, either supplied in a kit or individual items. One microlitre of cDNA was amplified in a total of 50 µL reaction mix containing 5 µL of 10 ×PCR Buffer, 1 µL of 10 mM dNTP mixture, 1.5 µL of 50 mM $MgCl_2$, 2 µL of each primer pair mix (10 µM each), 0.2 µL Platinum Taq DNA polymerase and 39.3 µL DEPC-treated water. PCR was performed by a Rotor-Gene 6000 (Corbett Research, Sydney, Australia; Qiagen). The conditions for amplification were initially denatured at 94° C., 2 minutes; 30-35 cycles of denaturation at 95° C., 10 seconds; annealing at 60° C., 20 seconds and synthesis at 72° C. for 20 seconds. A negative control without cDNA was included in all runs.

7) Concentration of PCR Products

Up to 4 µL of pooled PCR product was added to the 30K Amicon Ultra-4 filter unit (Millipore, North Ryde, NSW, Australia), a cellulose membrane for concentrating DNA, and spun on a Sigma 2-16PK swinging bucket rotor (John Morris Scientific, Chatswood, NSW, Australia) at 22° C., 5000 rpm (4025 g) for 10 minutes. The concentrated solute was collected at the bottom of the filter unit and stored at −20° C. for subsequent PCR.

8) DNA Size Confirmation and Quantitation

The concentrated PCR products were analysed on the MCE-202 MultiNA microchip automated electrophoresis instrument (Shimadzu Biotech, Rydalmere, NSW, Australia) for band size confirmation and concentration. All steps were followed according to the manufacture instructions with minor modification. Briefly, 6 µL of a ⅒ dilution (v/v) of concentrated PCR products (diluted in DEPC-treated water) were added to each well of the 96-well plate and sealed with adhesive PCR aluminium foil (Thermo Scientific, Integrated Sciences, NSW, Australia). The DNA-500 Separation Buffer (Shimadzu Biotech, Rydalmere, NSW, Australia) consisting of 10,000×SYBR Gold (Invitrogen), diluted at 1/100 dilution in TE (10 mM Tris-HCl, 1 mM disodium EDTA, pH8.0) (Sigma-Aldrich), was then used to separate the DNA samples through the microchips (Shimadzu Biotech, Rydalmere, NSW, Australia). The DNA band sizes and concentration were analysed alongside a 25 bp DNA ladder (Invitrogen), diluted 1:49 in TE (10 mM Tris-HCl, 1 mM disodium EDTA, pH8.0) (Sigma-Aldrich), and DNA-500 internal marker (Shimadzu Biotech, Rydalmere, NSW, Australia), respectively.

References:

Chomczynski, P., and Sacchi, N. (1987) Anal. Biochem. 162, 156.

Example 3 i) Standard Curve Preparation

Seven microlitres of concentrated DNA samples (i.e. 70, 90 or 170 bp products), in duplicate, were serially diluted in 1:1 (v/v) of TE (10 mM Tris-HCl, pH8.0, 1 mM EDTA) (Invitrogen), ranging from neat to 1/32 dilution, and 1.25 µM of EvaGreen dye (Biotium Inc, Hayward, Calif.; Jomar Biosciences, SA, Australia) in 0.2 mL PCR tubes containing a reaction volume of 50 µL TE (10 mM Tris-HCl, pH8.0, 1mM EDTA) (Invitrogen). The titration was performed in a Rotor-Gene 6000 (Corbett Research, Sydney, Australia; Qiagen). The conditions for cycling were initial denaturation at 94° C., 2 minutes; 15 cycles of denaturation at 95° C., 30 seconds; and fluorescent signals were acquired during every annealing step at 60° C. for 30 seconds. Two negative controls were included in each standard curve run—a non-template control and oligonucleotide at highest concentration without Evagreen dye. The DNA mixtures were stored at −20° C. for subsequent fluorescent repeat measurement.

Figure 2:
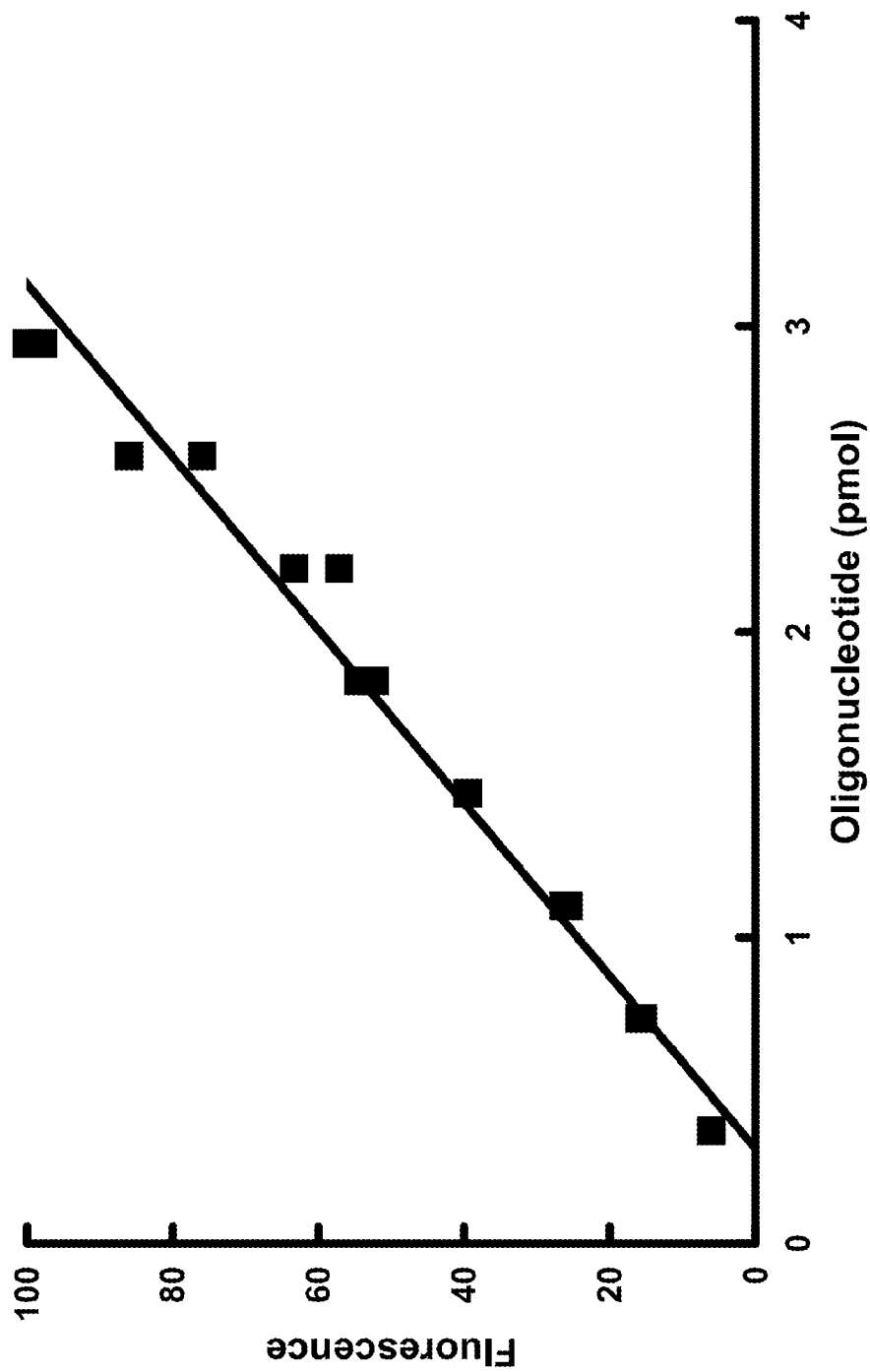
FIG. 2: Standard curve generated from the fluorescence data shown in FIG. 1.

The fluorescence for each concentration of reference oligonucleotide was obtained (see FIG. 1). The data was then plotted as fluorescence (Y axis) vs. reference oligonucleotide present in picomoles (X axis) (see FIG. 2) the curve of best fit was generated by least squares linear regression and a standard curve equation was generated.

ii) Calculations

Figure 3:
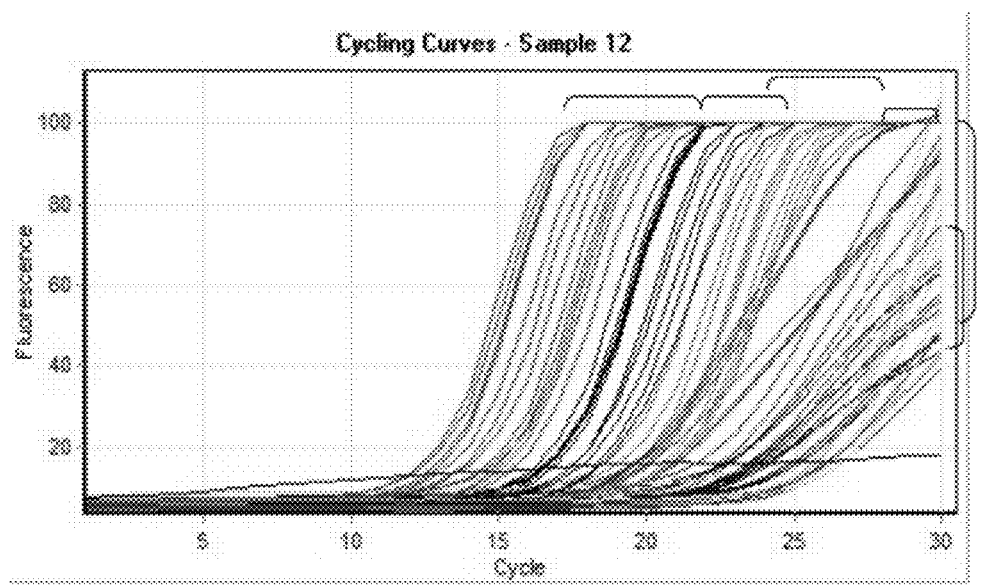
FIG. 3: Cycling curves for six genes (defined by the brackets). The cycles required for each gene to attain three given fluorescence levels f1, f2, f3 (e.g. 65, 60 and 55) are obtained from this data.

From the standard curve equation, calculate the picomole equivalents to 3 levels of fluorescence f1, f2 f3 (i.e. choose 3 thresholds) see FIG. 3.

From RT-PCR of test/target sample obtain:
efficiency for gene of interest (e)
cycles (c1, c2, c3) for each of the 3 levels of fluorescence (f1,f2,f3)
generate pmoles of gene of interest present in the sample [DNA(pmol)i] corresponding to f1,f2,f3 using the standard curve equation.

Calculate n (pmoles of gene of interest present at the start of the reaction) from $DNA(pmol)_i = n_i \times e^{ci}$ i.e. $n_i = DNA_i / e^{ci}$ Average $n_i$ to obtain moles of gene of interest present in sample.

Figure 4:
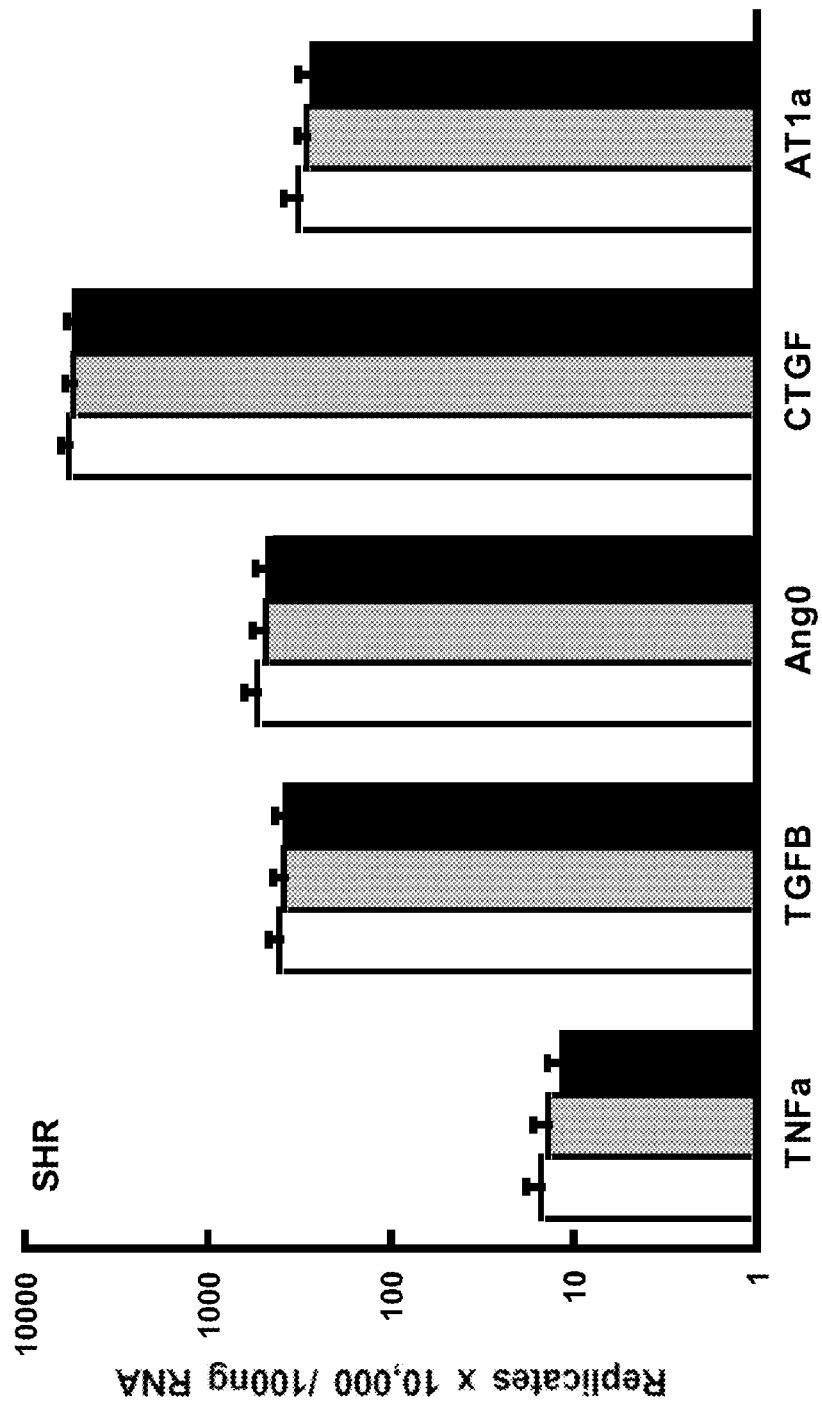
FIG. 4: Expression of five genes of interest in the hearts of SHR rats. The expression of each gene of interest was calculated using reference oligonucleotide (open bars), reference oligonucleotide plus 20 base pairs (hatched bars) and reference oligonucleotide plus 100 base pairs (solid bars). Increasing the reference oligonucleotide length did not significantly affect the calculation of the expression of the gene of interest. TNFα $p=0.3946$; TGFβ $p=0.7151$; Ang0 $p=0.6158$; CTGF $p=0.4955$ and AT1a $p=0.5589$, for reference oligonucleotide vs. Reference oligonucleotide plus 20 and 100 base pairs (ANOVA).

Correct for total RNA present in each reaction and express $n_i$ as pmoles/100 ng total RNA. Multiplication by Avagadro's number allows it to be alternatively expressed as replicates/100 ng RNA (see FIG. 4).

Example 4

Thus, FIG. 1 shows the fluorescence for each concentration of reference oligonucleotide performed in duplicate. The data plotted as fluorescence (y axis) vs. reference oligonucleotide present expressed in pmol (x axis) in FIG. 2 allows the calculation, by least squares regression, of the equation defining this relationship. Substitution of f1,f2,f3 (obtained from the plot of fluorescence for each gene of interest vs. cycle number see FIG. 3) into the standard curve equation results in calculated pmoles of gene of interest ($DNA_i$) present at cycles c1,c2,c3. The pmoles of gene of interest present at time zero can then be calculated as above and corrected for total RNA and expressed as Replicates after multiplication by Avagadro's number.

Comparison of reference oligonucleotides of differing lengths as standards for the calculation of n. Three oligonucleotides differing in length by 20 and 100 base pairs were used to generate three standard curves as described under i) standard curve preparation method. Then five genes of interest were quantified independently using each standard curve in turn as described under ii) calculations. The results obtained for each gene by the three curves were compared by ANOVA, significant difference was set at the 0.05 level (see FIG. 4). The expression of the genes of interest did not differ significantly between the three groups. Thus variations in length of a reference oligonucleotide up to 100 base pairs did not affect the calculation of the gene of interest.

Figure 5:
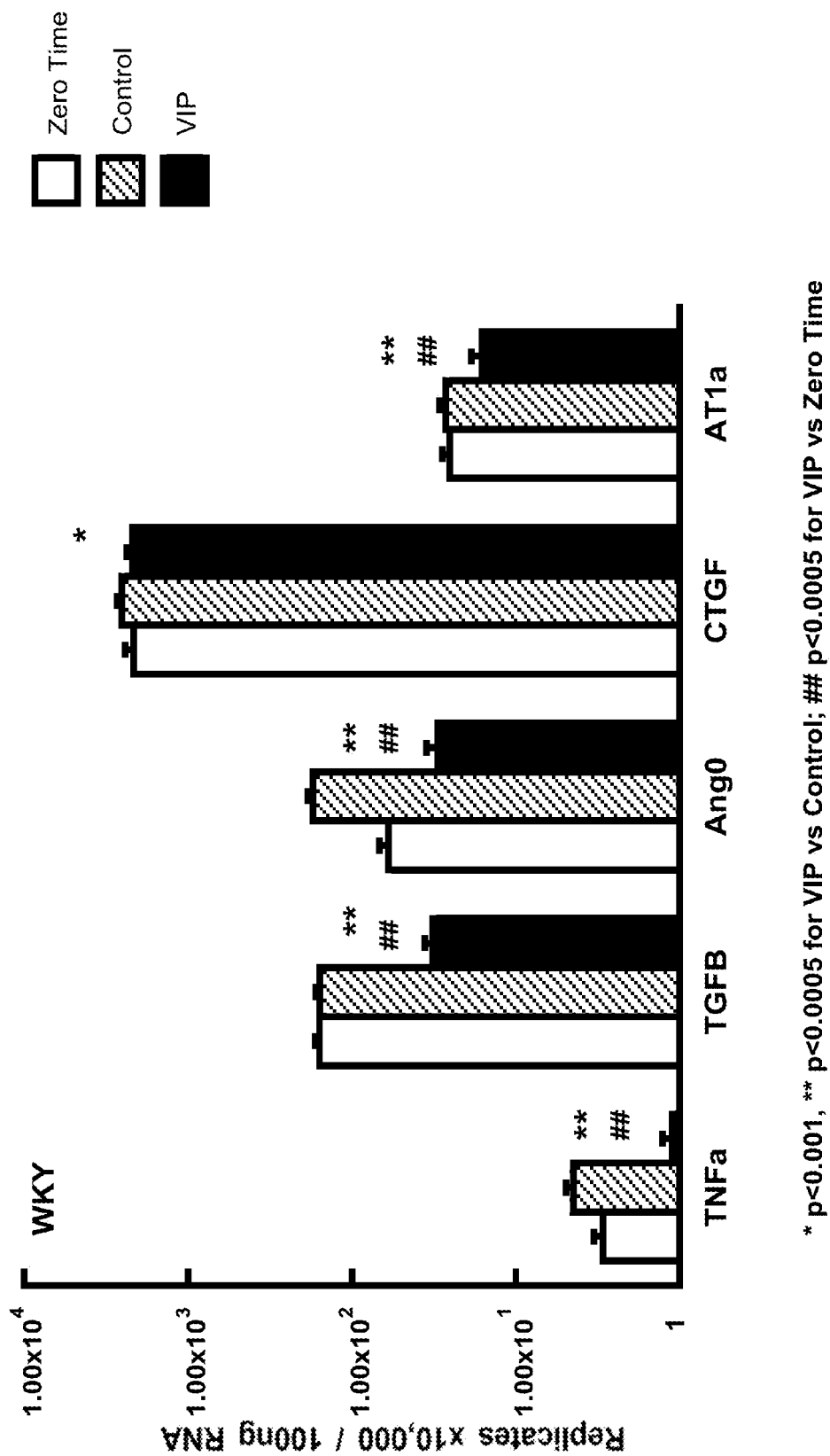
FIG. 5: Expression of five genes of interest in the hearts of WKY rats on a high salt diet in 3 experimental groups—a zero time control (14 week old) open bars, after 4 weeks control vehicle infusion (18 weeks old) hatched bars and after 4 weeks treatment with VIP (18 weeks) solid bars.

Application to the Experimental situation (see FIG. 5).

Five genes of interest were measured in the hearts of WKY rats in 3 experimental groups—Zero Time Control (open bars), Vehicle Control (hatched bars) and following treatment with VIP (solid bars) using the method described above.

Stability and Reproducibility of Standard Curves

Figure 6:
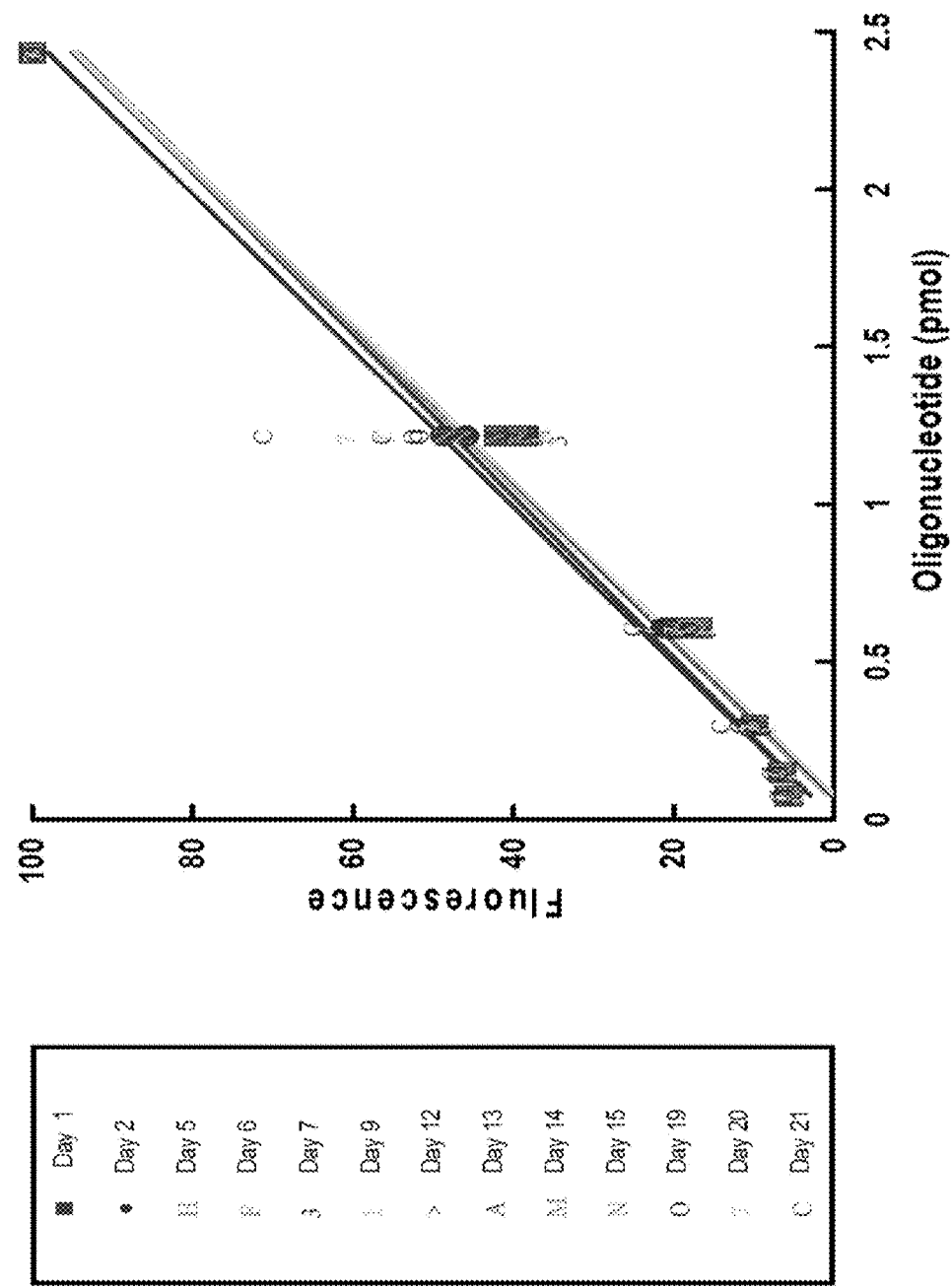
FIG. 6: Standard curves generated over 3 weeks. Reference oligonucleotide dye reaction mixtures were frozen and stored at −20° C. between runs thawed for each run and re-frozen. As can be seen the standard curves generated are stable over time and repeated freezing and re-thawing.
Figure 7A:
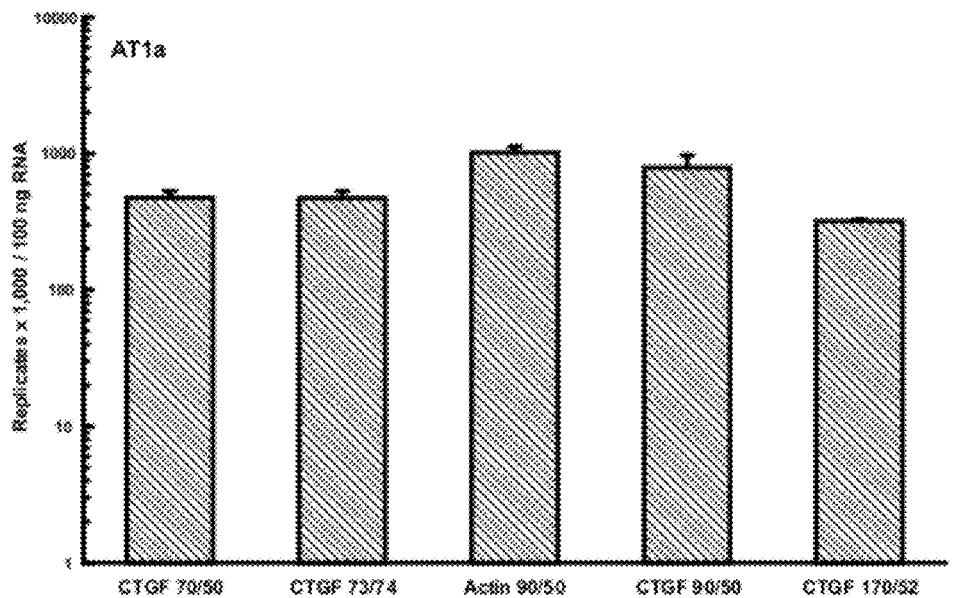
FIGS. 7A-F: Quantification results for six genes of interest (angiotensinogen, TGFβ, TNFα, CTGF, At1a and NONO) using 5 reference oligonucleotides ranging from 70 to 170 base pairs in length and varying in GC content from 50% to 74%. The reference oligonucleotides shown in these examples are CTGF 70 base pairs, 50% GC content (CTGF 70/50), CTGF 73 base pairs, 74% GC content (CTGF73/74), β Actin 90 base pairs 50% GC content (Actin 90/50), CTGF 90 base pairs 50%, GC content (CTGF 90/50) and CTGF 170 base pairs 52%, GC content (CTGF 170/52).
Figure 7B:
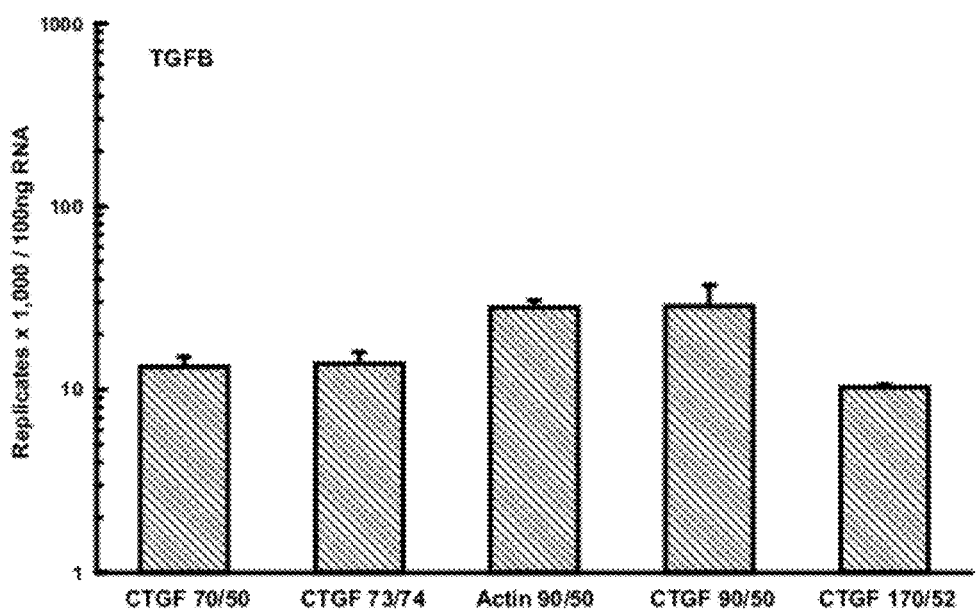
Figure 7C:
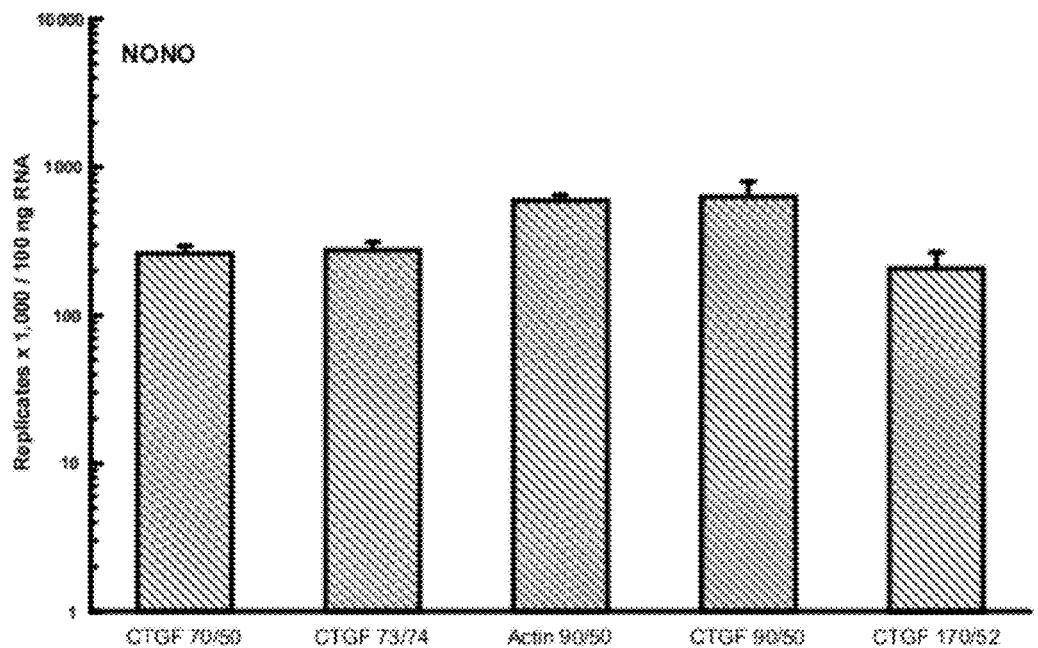
Figure 7D:
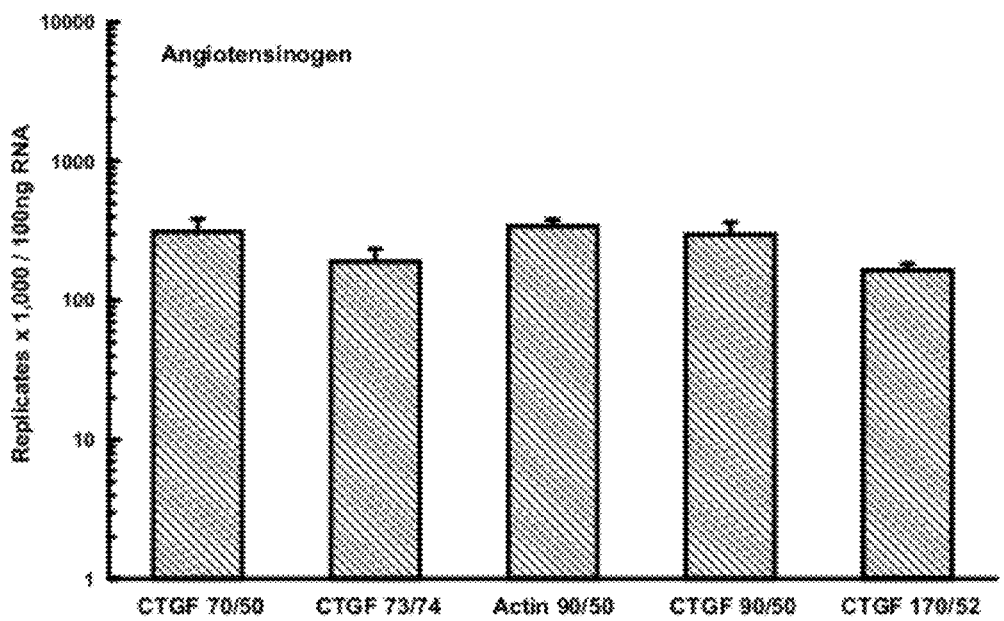
Figure 7E:
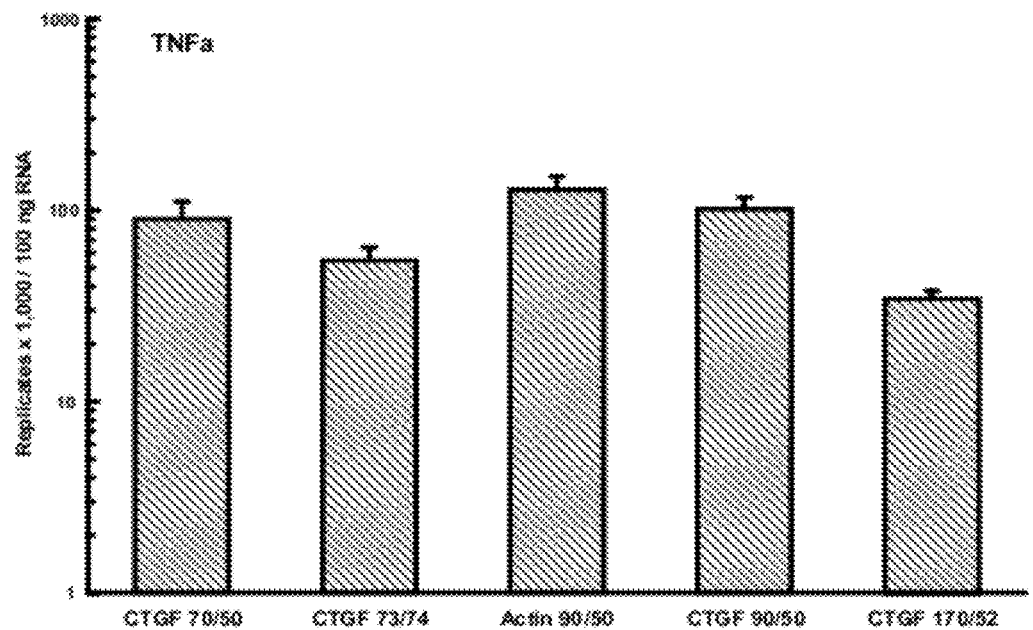
Figure 7F:
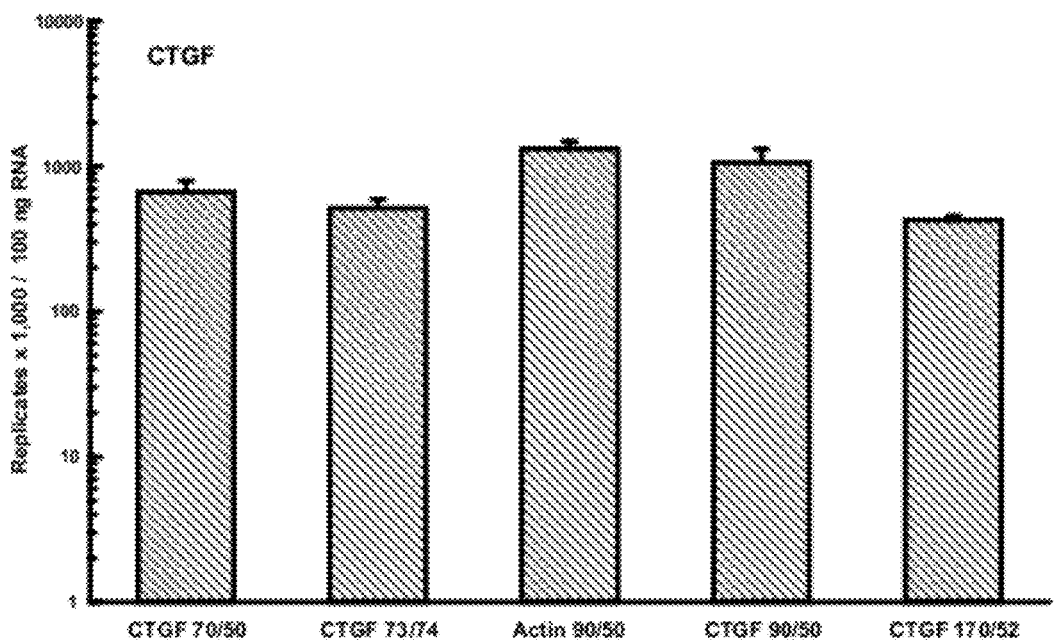
Figure 8A:
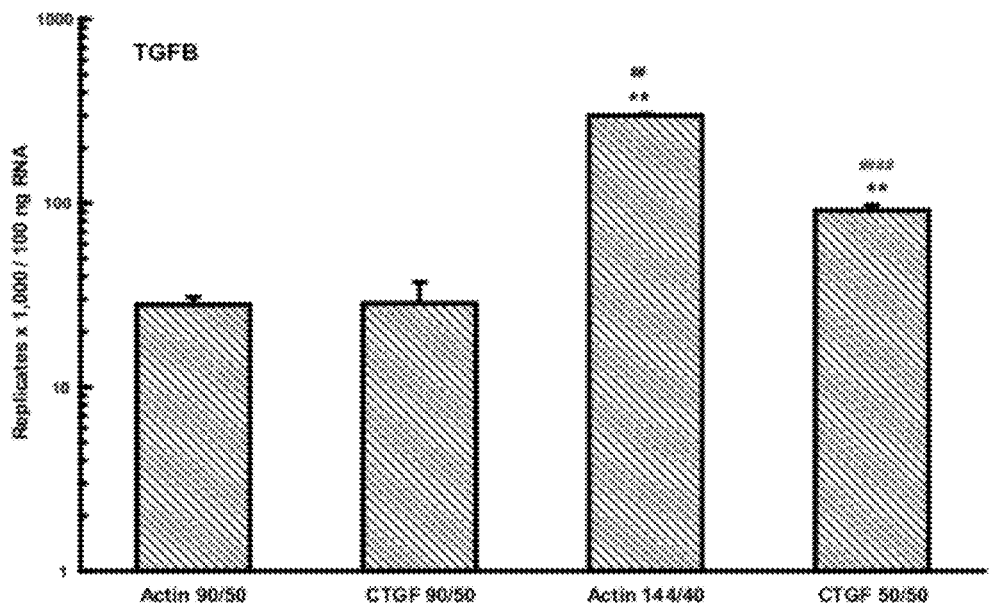
FIGS. 8A-F: Shows quantification results for six genes of interest (angiotensinogen, TGFβ, TNFα, CTGF, At1a and NONO) using 4 reference oligonucleotides ranging from 50 to 144 base pairs in length and varying in GC content from 40% to 50%. The reference oligonucleotides shown in these examples are Actin 144/40 (β Actin 144 base pairs, 40% GC content), CTGF 50/50 (CTGF 50 base pairs, 50% GC content), Actin 90/50 (β Actin 90 base pairs, 50% GC content) and CTGF 90/50 (CTGF 90 base pairs, 50% GC content). *$p<0.005$, **$p<0.0005$ vs Actin 90/50; #$p<0.01$, ##$p<0.005$, ###$p<0.001$ and ####$p<0.0005$ vs CTGF 90/50.
Figure 8B:
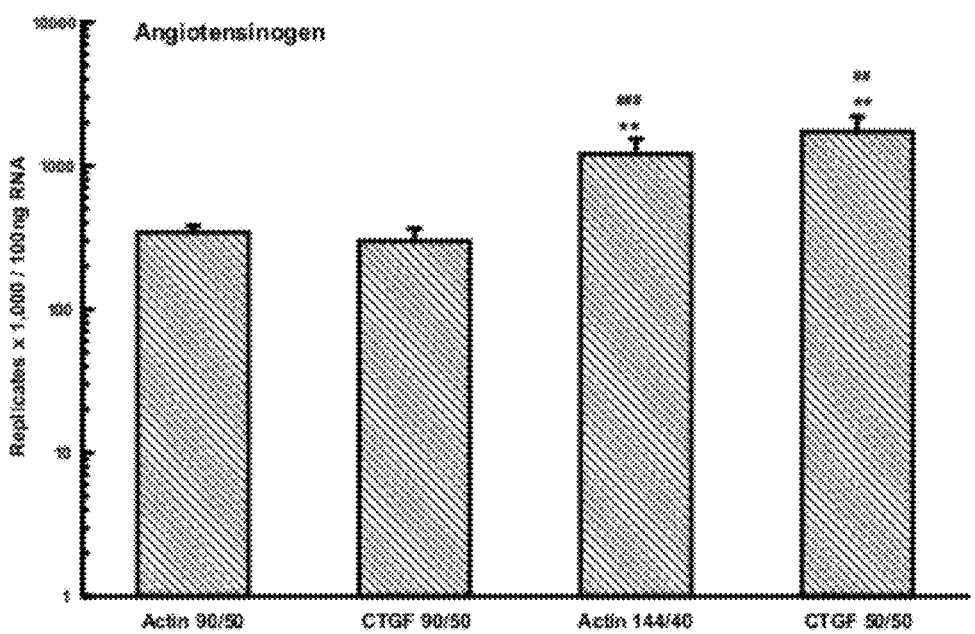
Figure 8C:
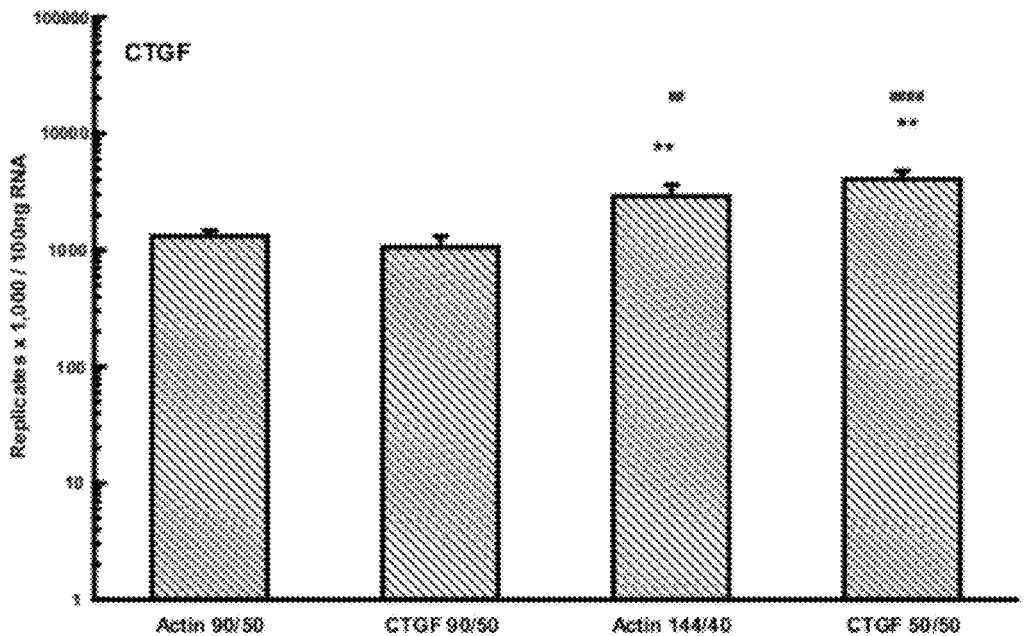
Figure 8D:
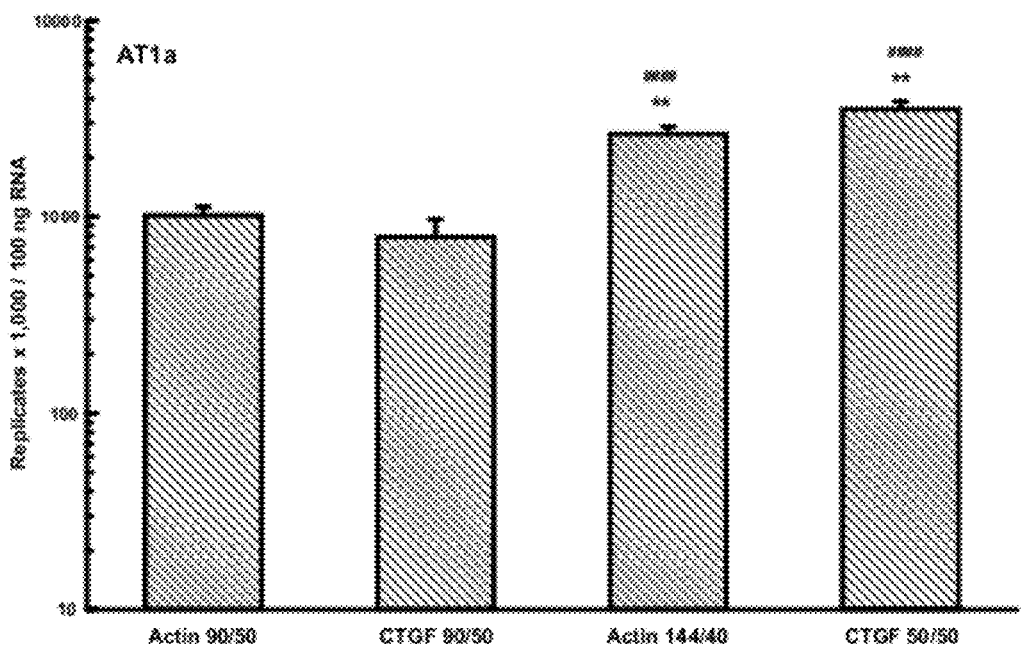
Figure 8E:
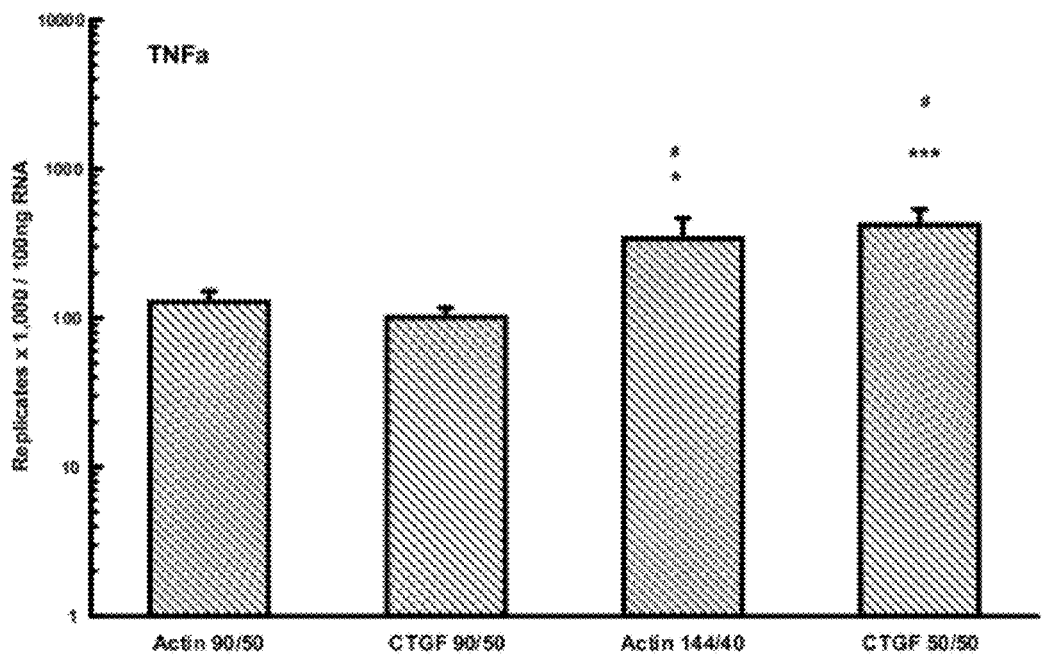
Figure 8F:
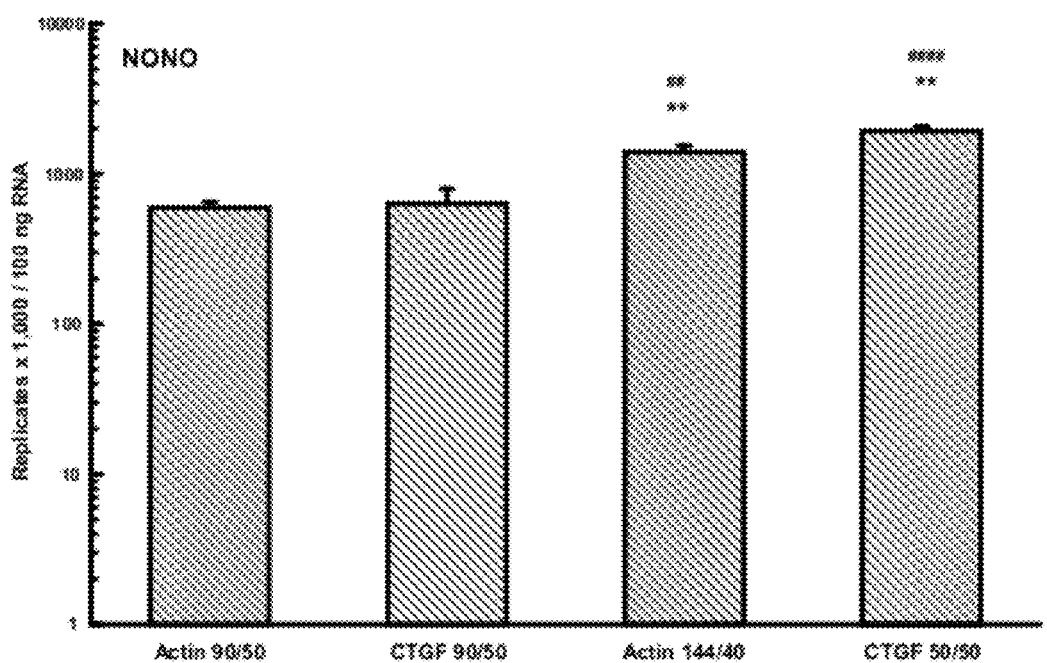

The tubes containing various concentrations of reference oligonucleotide and EvaGreen dye had their fluorescence measured after repeated freeze thawing over a three week period. The levels of fluorescence were stable for each concentration. Thus one standard may be used as the quantification standard for a large number of rt-PCR runs providing that the same batch of dye has been employed and that dye concentration has not varied between the runs (see FIG. 6).

Example 5

Reference oligonucleotides varying in length from 50 to 170 base pairs and in GC content from 40 to 75% were formulated from various sections of CTGF, a_Actin and 0 Actin.

Reference oligonucleotides were prepared as described under Example 2 and standard curves prepared as described under Example 3. Primers generating the reference oligonucleotides (50 to 170bp) were designed based on sequences published by the NCBI Genbank for rat mRNA for CTGF (Accession No. AB023068) and rat mRNA for αActin and βActin (Accession No. NM —019183 and BC063166 respectively), See Table 2.

Six Genes of interest (AT1a, Angiotensin, TGFβ, TNFa, NONO and CTGF) were quantified independently using each standard curve in turn as described under ii) calculations. The results obtained for each gene by the three curves were compared by ANOVA.

TABLE 2

Primer Sequences used for PCR and Construction of Standard Curves

| Primer | Sequence (5' to 3') | Reference (NCBI GenBank Locus) |
| --- | --- | --- |
| 144 bp αActin (40% GC) | ATGCAAAAGGAAATAACTGCAC (forward) (SEQ ID NO: 7) TTGCTTGCTGATCCACATTT (reverse) (SEQ ID NO: 8) | NM_019183 |
| 90 bp βActin (50% GC) | TTCCTGGGTATGGAATCCTG (forward) (SEQ ID NO: 9) GGCATAGAGGTCTTTACGGATG (reverse) (SEQ ID NO: 10) | BC063166 |
| 50 bp CTGF (50% GC) | AGAGTCGTCTCTGCATGGTC (forward) (SEQ ID NO: 11) GTTTTCCTCTAGGTCAGCTTC (reverse) (SEQ ID NO: 12) | AB023068 |
| 70 bp CTGF (50% GC) | AAGATGGTGCACCCTGTGTCTTC (forward) (SEQ ID NO: 13) TGCAACTGCTTTGGAAGGACTC (reverse) (SEQ ID NO: 14) | AB023068 |

TABLE 2-continued

Primer Sequences used for PCR and Construction of Standard Curves

| Primer | Sequence (5' to 3') | Reference (NCBI GenBank Locus) |
| --- | --- | --- |
| 90 bp CTGF (50% GC) | AAAGATGGTGCACCCTGTGTCTT (forward) (SEQ ID NO: 15) CAGGCAAGTGCACTGGTATTTG (reverse) (SEQ ID NO: 16) | AB023068 |
| 170 bp CTGF (52% GC) | AATGCTGTGAGGAGTGGGTGT (forward) (SEQ ID NO: 17) CATCCCACAGGTCTTAGAACAGG (reverse) (SEQ ID NO: 18) | AB023068 |
| 73 bp CTGF (74% GC) | TGCCTGGATGGGGCCGTGGGCTG (forward) (SEQ ID NO: 19) AGGGGCAGTCAGGGCTGGGCAGG (reverse) (SEQ ID NO: 20) | AB023068 |
| 120 bp CTGF (70% GC) | TCGGTGGGTCCGTGTACCGCAGC (forward) (SEQ ID NO: 21) TGGGCAGGCGCACGTCCATGCT (reverse) (SEQ ID NO: 22) | AB023068 |

The results are shown in FIGS. 7A-F and FIGS. 8A-F. In these experiments the quantification of the genes of interest was only affected (resulted in significantly higher values of replicates of gene of interest) by reference oligonucleotide having a length of 50 bp and GC content of 40%. Reference oligonucleotides of greater length and higher GC content, all with no apparent limitation as to the upper limit of either parameter, all provided accurate quantification of the gene of interest. From these experiments it can be concluded that the lower limit of length of a reference oligonucleotide, useful in the method of the present invention, is 60 bp and the GC content of 45%. These values may represent the lower limits of the useful range of these values. The upper limits can be set depending on the requirements. If a single universal reference oligonucleotide is to be used, for convenience the length can be set at 100 bp and GC content at 50%. From the data provided herein any alternative suitable length and GC content for the reference oligonucleotide may also be selected Example 6

Each of these reference oligonucleotides were used to in turn to quantify nine genes of interest (angiotensinogen, TNFα, TGFβ, CTGF, NONO MMP2, MMP9 and TIMP1) whose gene products varied from 80 to 120 base pairs (See Table 3 for amplicon sequences).

TABLE 3

Amplicon sequences for genes of interest

| Gene of Interest | Amplicon | Size (bp) |
| --- | --- | --- |
| Angiotensinogen (AGT) | TCTTCCCTCGCTCTCTGGACTTATCCACTGACCCAGT TCTTGCTGCCCAGAAAATCAACAGGTTTGTGCAGGC TGTGACAGG (SEQ ID NO: 23) | 82 |
| TNF-α | TGTCTGAGACCAACTCAACCCAGAAAAACAAAATGG CCCTTAACTCTTCTGCTGAAGATGGTATCAAAAGAAT CCAAGATGACTGCCCCA (SEQ ID NO: 24) | 82 |

TABLE 3-continued

Amplicon sequences for genes of interest

| Gene of Interest | Amplicon | Size (bp) |
|---|---|---|
| TGF-β1 | CTACTGCTTCAGCTCCACAGAGAAGAACTGCTGTGT ACGGCAGCTGTACATTGACTTTAGGAAGGACCTGGG TTGGAAGT (SEQ ID NO: 25) | 80 |
| CTGF | CTGTTGGCGAACAAATGGCCTTTATTAAGAAATGGCT TGCTCAGGGTAACTGGTCAGATTTCCACGAGGAAGT GTTTGCTGCTTCTTTGACTATGACT (SEQ ID NO: 26) | 98 |
| NFκB | TCTGATGAACATACACCAGTAGAGGATGAAGAACCA AAGAAAAGCACTACTTCAGCATCTAGTTCGGAAGAT GATAAGAAGAAGAAAAGGAAATCTAGTCGTTCAAAA GAAAGAGCCAAG (SEQ ID NO: 27) | 120 |
| AT1a | TGTCTGAGACCAACTCAACCCAGAAAAACAAAATGG CCCTTAACTCTTCTGCTGAAGATGGTATCAAAAGAAT CCAAGATGACTGCCCCA (SEQ ID NO: 28) | 90 |
| NONO | AAGCAGGCGAAGTTTTCATTCATAAGGATAAAGGCTT TATTCGCTTGGAAACACGAACCCTAGCGGAAATTGC CAAAGTGGAGCTGGAC (SEQ ID NO: 29) | 95 |
| MMP2 | CTGGCACTTTTACTACTTTAGCTGTTTGCTTTGTTTG CCCTTTGCTGTTTGGTTCAACCTTTTCAGTTTTCCAC CACACTGCATTTTTCTCACCG (SEQ ID NO: 30) | 95 |
| MMP9 | CCCCCAACCTTTACCAGCTACTCGAACCAATCAGCT TGTCTGTAGTTGTATACACATCCAAGCCTGTGGTTG GTCAGAAGACAACTTTGTAGG (SEQ ID NO: 31) | 93 |
| TIMP1 | GGGTGTGCACAGTGTTTCCCTGTTCAGCCATCCCTT GCAAACTGGAGAGTGACAGTCATTGCTTGTGGACAG ATCAGATCCTCATGGGCT (SEQ ID NO: 32) | 90 |

The nine genes of interest were measured in the hearts of SHR rats (n=6) in 4 experimental groups —Zero Time Control (open bars), Vehicle Control (hatched bars) and following treatment with VIP (solid bars) and enalapril treatment (cross hatched bars), using the method described above.

Figure 9A:
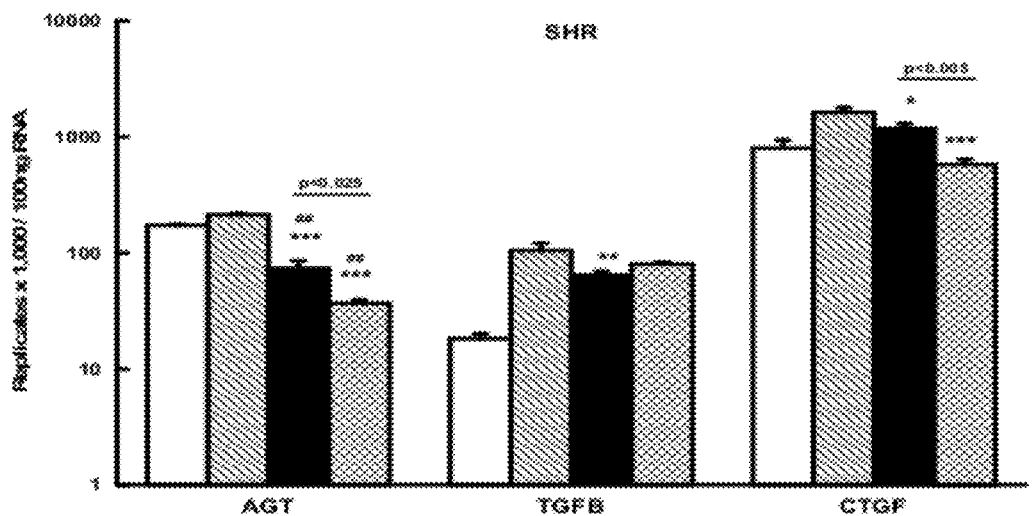
FIG. 9A: Effects of VIP or enalapril treatment on angiotensinogen (AGT), TGFβ and CTGF expression in SHR, zero Time Control (open bars), vehicle control (hatched bars), VIP infusion (solid bars) and enalapril treatment (cross hatched bars). *$p<0.05$, $p<0.025$, *$p<0.0005$ for VIP or enalapril vs vehicle control. #$p<0.001$ ##$p<0.0005$ for VIP or enalapril vs zero time control.
Figure 9B:
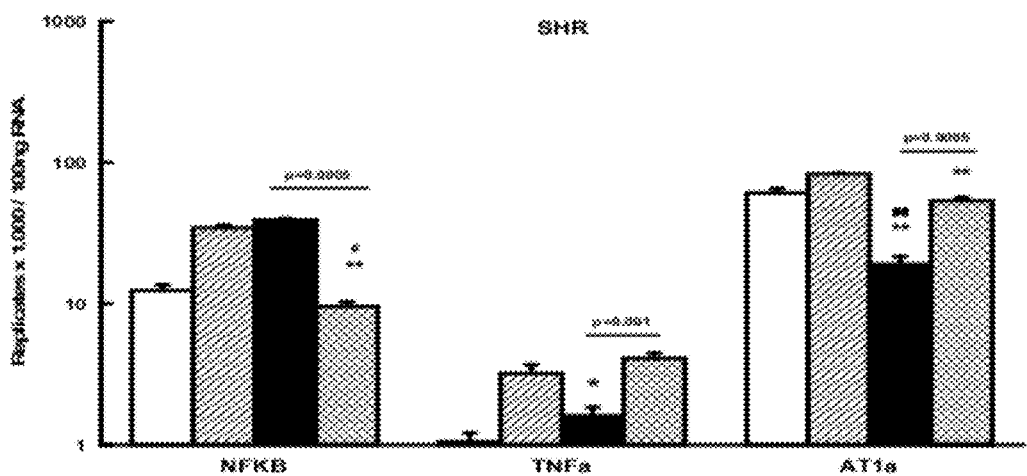
FIG. 9B: Effect of treatment with VIP or enalapril on NF Kappa B, TNFα and AT1a receptor expression in SHR. *p<0.01 **p<0.0005 for VIP or enalapril vs Vehicle Control; #p<0.05, ##p<0.0005 for VIP or enalapril vs zero time control.
Figure 9C:
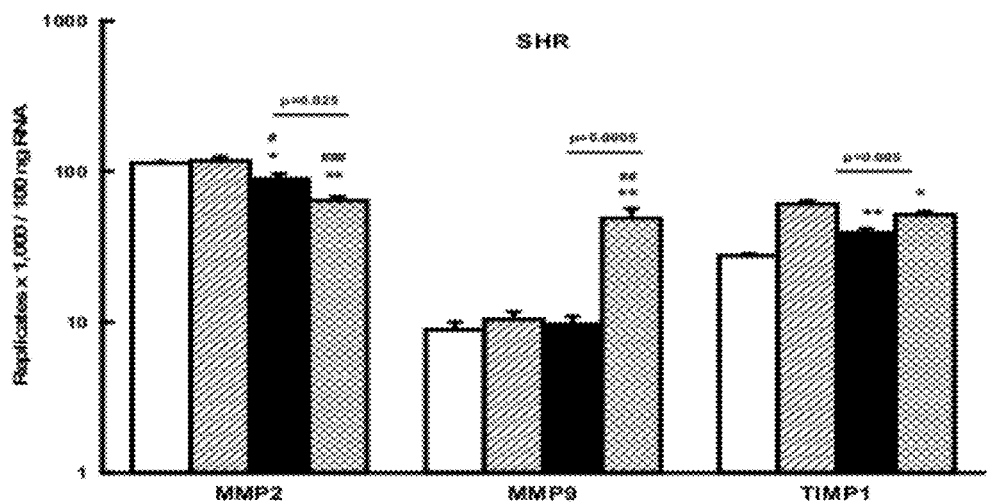
FIG. 9C: Effect of treatment with VIP or enalapril on metalloproteinase and TIMP expression in SHR. *p<0.025, **p<0.0005 for VIP or enalapril vs vehicle control; #p<0.01, ##p<0.001, ###p<0.0005 VIP or enalapril vs zero time control. Values are mean±sem for n=6 rats.

The results are shown in FIGS. 9A-C. These results demonstrate the ability of the reference oligonucleotide method to accurately quantify the amount of nucleic acid products and thus elucidate accurately the changes in gene expression brought about by treatment of hypertensive rats with compounds such as VIP and enalapril. The method provides the sensitivity to delineate statistically significant differences between treated and control animals as well as the efficacy of different treatments with respect to regulation of gene expression by different treatments. Whereas particular animal studies were used as a convenient example of how the method performs in a particular experimental situation, the same quantification principles and method is applicable to any such situation in which accurate quantification of nucleic acid products, unaffected by any undesirable changes in housekeeping genes and the like, is required.

Similar experiments conducted using dyes SYBR green I, SYBR green II, CYBR gold, Evagreen, oxazole yellow, thiazole orange, picogreen, TOTO and BEBO, and the protocols described above, yielded similar results.

It will be appreciated that the illustrated method provides an improved method of quantifying gene expression products without normalisation to a housekeeping gene or a synthetic gene, or the need to co-amplify the housekeeping/synthetic reference genes with the target sequence.

Although the invention has been described with reference to specific examples, it will be appreciated by those skilled in the art that the invention may be embodied in many other forms.

The claims defining the invention are as follows:

1. A method for quantifying nucleic acids comprising:
   a) labelling a universal reference oligonucleotide having a predetermined length with a detectable marker;
   b) generating a standard curve using serial dilutions of the labelled universal reference oligonucleotide by plotting the intensity of the detectable marker against concentration of labelled universal reference oligonucleotide;
   c) amplifying a target nucleic acid in the presence of the detectable marker which labels the amplified target nucleic acid,
   d) comparing in real time the intensity of the detectable marker associated with the labelled amplified target nucleic acid, with the standard curve and determining the quantity of the amplified target nucleic acid, wherein said labelled universal reference oligonucleotide is not amplified during generation of the standard curve.

2. The method according to claim 1, wherein the detectable marker is a dye.

3. The method according to claim 2, wherein the dye binds to dsDNA.

4. The method according to claim 3, wherein the dye is an intercalating dye.

5. The method according to claim 2, wherein the dye is a fluorescent dye.

6. The method according claim 1, wherein the universal reference oligonucleotide has a length of about 60bp or greater.

7. The method according to claim 1, wherein the universal reference oligonucleotide has a GC content of 45% or greater.

8. The method according to claim 1 wherein the universal reference oligonucleotide has a length of about 60bp to about 170bp.

9. The method according to claim 1 wherein the universal reference oligonucleotide has a GC content of about 45% to about 75%.

10. The method according to claim 1, wherein the universal reference oligonucleotide has a length of about 100bp and GC content of about 50%.

11. The method according to claim 1, wherein the universal reference oligonucleotide is longer or shorter than the target nucleic acid.

12. The method according to claim 1, wherein a single standard curve is used for multiple target nucleic acid amplifications and quantifications.

* * * * *